(12) United States Patent
Sakai et al.

(10) Patent No.: US 10,149,615 B2
(45) Date of Patent: Dec. 11, 2018

(54) FUNDUS IMAGING APPARATUS THAT DETERMINES A STATE OF ALIGNMENT

(71) Applicant: KABUSHIKI KAISHA TOPCON, Itabashi-ku (JP)

(72) Inventors: Jun Sakai, Kuki (JP); Makoto Fujino, Itabashi-ku (JP); Keisuke Arima, Sakura (JP); Ryoichi Yahagi, Yamagata (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 14/648,575

(22) PCT Filed: Nov. 27, 2013

(86) PCT No.: PCT/JP2013/081856
§ 371 (c)(1),
(2) Date: May 29, 2015

(87) PCT Pub. No.: WO2014/084231
PCT Pub. Date: Jun. 5, 2014

(65) Prior Publication Data
US 2015/0313467 A1  Nov. 5, 2015

(30) Foreign Application Priority Data

Nov. 30, 2012 (JP) ................................. 2012-262241
Nov. 30, 2012 (JP) ................................. 2012-262727

(51) Int. Cl.
*A61B 3/12* (2006.01)
*A61B 3/00* (2006.01)
(Continued)

(52) U.S. Cl.
CPC .............. *A61B 3/12* (2013.01); *A61B 3/0041* (2013.01); *A61B 3/0091* (2013.01); *A61B 3/102* (2013.01);
(Continued)

(58) Field of Classification Search
CPC ......... A61B 3/12; A61B 3/102; A61B 3/1025; A61B 3/152; A61B 3/15
(Continued)

(56) References Cited

U.S. PATENT DOCUMENTS 4,626,089 A * 12/1986 Takahashi ................ A61B 3/12
351/206
6,027,216 A *  2/2000 Guyton .................. A61B 3/113
351/200
(Continued)

FOREIGN PATENT DOCUMENTS

JP  H01-113025 A  5/1989
JP  06 110947     4/1994
(Continued)

OTHER PUBLICATIONS

Partial Supplementary European Search Report dated Jun. 8, 2016 in Patent Application No. 13858552.6.
(Continued)

*Primary Examiner* — Zachary Wilkes
(74) *Attorney, Agent, or Firm* — Oblon, McClelland, Maier & Neustadt, L.L.P.

(57) ABSTRACT

A fundus imaging apparatus includes a scanning optical system, a control circuit, and an image forming unit. The scanning optical system scans a fundus of a subject's eye with light from a light source, and receives return light from the fundus by a light receiver. The control circuit controls the scanning optical system such that a scanning locus is formed by the light in the fundus. The image forming unit forms an
(Continued)

image of the fundus based on a light receiving signal from the light receiver and a position of the scanning locus. The control circuit is capable of performing an alignment mode, in which the control circuit controls the scanning optical system to project an alignment indicator for aligning the scanning optical system with the subject's eye on the fundus based on the light from the light source.

9 Claims, 44 Drawing Sheets

(51) Int. Cl.
    *A61B 3/15*     (2006.01)
    *A61B 3/10*     (2006.01)
(52) U.S. Cl.
    CPC .......... *A61B 3/1025* (2013.01); *A61B 3/1208* (2013.01); *A61B 3/152* (2013.01)
(58) Field of Classification Search
    USPC ........................................................ 351/208
    See application file for complete search history.

(56) References Cited

U.S. PATENT DOCUMENTS

| | | | |
|---|---|---|---|
| 6,299,307 B1 * | 10/2001 | Oltean | A61B 3/113 351/210 |
| 7,643,154 B2 * | 1/2010 | Kikawa | A61B 3/10 356/497 |
| 7,651,223 B2 | 1/2010 | Ichikawa | |
| 7,766,903 B2 * | 8/2010 | Blumenkranz | A61F 9/008 606/10 |
| 7,980,696 B1 | 7/2011 | Taki et al. | |
| 2005/0286019 A1 | 12/2005 | Wiltberger et al. | |
| 2006/0195076 A1 | 8/2006 | Blumenkranz et al. | |
| 2008/0024721 A1 | 1/2008 | Ueno et al. | |
| 2009/0093798 A1 | 4/2009 | Charles | |
| 2009/0303438 A1 | 12/2009 | Yamada et al. | |
| 2010/0191226 A1 | 7/2010 | Blumenkranz et al. | |
| 2010/0283970 A1 | 11/2010 | Sekiguchi et al. | |
| 2011/0150293 A1 | 6/2011 | Bower et al. | |
| 2011/0178511 A1 | 7/2011 | Blumenkranz et al. | |
| 2011/0178512 A1 | 7/2011 | Blumenkranz et al. | |
| 2011/0245816 A1 | 10/2011 | Abe | |
| 2012/0316545 A1 | 12/2012 | Blumenkranz et al. | |
| 2013/0003018 A1 | 1/2013 | Utagawa et al. | |
| 2013/0023864 A1 | 1/2013 | Blumenkranz et al. | |
| 2013/0169931 A1 | 7/2013 | Lee et al. | |
| 2013/0197634 A1 | 8/2013 | Palanker et al. | |
| 2013/0304046 A1 | 11/2013 | Charles | |
| 2014/0094784 A1 | 4/2014 | Charles | |
| 2014/0094785 A1 | 4/2014 | Charles | |
| 2014/0228826 A1 | 8/2014 | Blumenkranz et al. | |
| 2014/0228827 A1 | 8/2014 | Blumenkranz et al. | |
| 2014/0316386 A1 | 10/2014 | Blumenkranz et al. | |
| 2015/0038951 A1 | 2/2015 | Blumenkranz et al. | |
| 2015/0038952 A1 | 2/2015 | Blumenkranz et al. | |
| 2015/0141968 A1 | 5/2015 | Blumenkranz et al. | |
| 2015/0265465 A1 | 9/2015 | Charles | |
| 2015/0366712 A1 | 12/2015 | Palanker et al. | |
| 2016/0074214 A1 | 3/2016 | Palanker et al. | |
| 2016/0074218 A1 | 3/2016 | Palanker et al. | |
| 2016/0074229 A1 | 3/2016 | Palanker et al. | |

FOREIGN PATENT DOCUMENTS

| | | |
|---|---|---|
| JP | H09-234186 A | 9/1997 |
| JP | H 10-151114 A | 6/1998 |
| JP | H11-009553 A | 1/1999 |
| JP | 11-253403 A | 9/1999 |
| JP | 2000-189386 A | 7/2000 |
| JP | 2000-237168 A | 9/2000 |
| JP | 2001-161646 A | 6/2001 |
| JP | 2002-078682 A | 3/2002 |
| JP | 2002 369801 | 12/2002 |
| JP | 2003-000546 A | 1/2003 |
| JP | 2004-290535 A | 10/2004 |
| JP | 2004-358111 A | 12/2004 |
| JP | 2005 279121 | 10/2005 |
| JP | 2006-501534 A | 1/2006 |
| JP | 2007-097820 A | 4/2007 |
| JP | 2008-061848 A | 3/2008 |
| JP | 2008-526384 A | 7/2008 |
| JP | 2008-289642 A | 12/2008 |
| JP | 2009-183332 A | 8/2009 |
| JP | 2009-291252 A | 12/2009 |
| JP | 2010-000191 A | 1/2010 |
| JP | 2010-094381 A | 4/2010 |
| JP | 2010-259606 A | 11/2010 |
| JP | 2011-501985 A | 1/2011 |
| JP | 2011-24930 A | 2/2011 |
| JP | 2011 147609 | 8/2011 |
| JP | 2011 212203 | 10/2011 |
| JP | 2011 244917 | 12/2011 |
| JP | 2012-75640 A | 4/2012 |
| JP | 2012 075641 | 4/2012 |
| JP | 2012-176162 | 9/2012 |
| JP | 2012-200292 A | 10/2012 |

OTHER PUBLICATIONS

International Search Report dated Jan. 21, 2014 in PCT/JP13/081856 filed Nov. 27, 2013.
Extended European Search Report dated Nov. 21, 2016 in Patent Application No. 13858552.6.
Japanese Office Action issued in Japanese Patent Application No. 2016-055371 dated May 1, 2018 (w/ English Translation).
Office Action dated Jul. 28, 2017, in Japanese Patent Application No. 2016-055371 (English-language translation only).
Office Action dated Jul. 31, 2017, in Japanese Patent Application No. 2016-107999 (English-language translation only).
Office Action dated Aug. 2, 2017, in Japanese Patent Application No. 2013-244540 (English-language translation only).
Office Action dated Sep. 14, 2017, in Japanese Patent Application No. 2014-549848 (English-language translation only).
Japanese Office Action dated Mar. 13, 2018, issued in Japanese Patent Application No. 2016-107999 (with English translation).
U.S. Office Action issued in U.S. Appl. No. 15/335,861 dated May 25, 2018.
Japanese Office Action issued in Japanese Patent Application 2017-227088 dated Aug. 22, 2018 (w/ English Abstract).

* cited by examiner

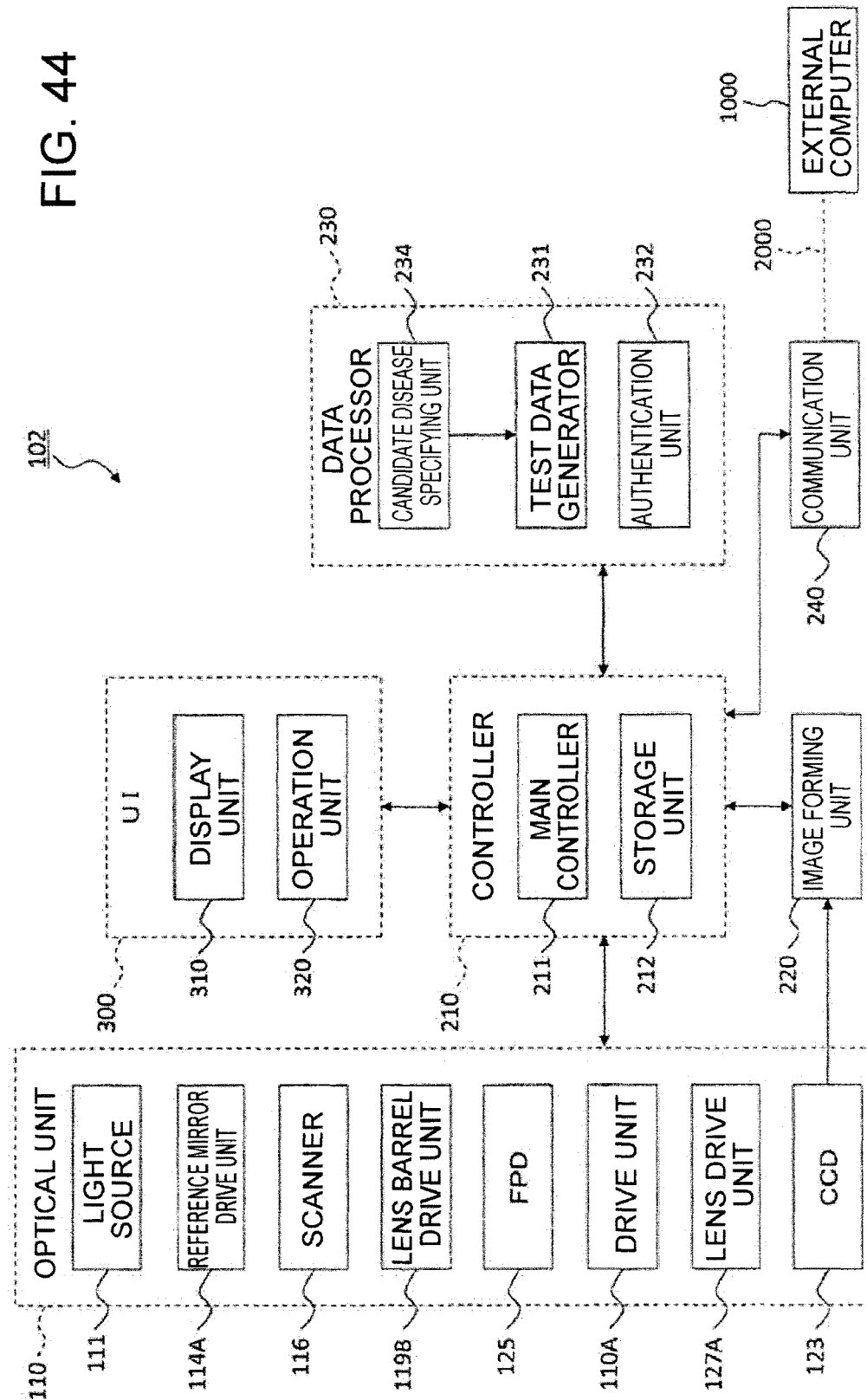

FUNDUS IMAGING APPARATUS THAT DETERMINES A STATE OF ALIGNMENT

FIELD

The present invention relates to a fundus imaging apparatus.

BACKGROUND

There are generally known fundus imaging apparatuses (optical scanning ophthalmoscope, optical coherence tomography apparatus, etc.) that scan an eye fundus with laser light and detect its return light to acquire a fundus image (see, for example, Patent Document 1). Among such fundus imaging apparatuses are those that perform alignment of the apparatus body by projecting an alignment indicator onto the subject's eye (see, for example, Patent Document 2).

Besides, there are known fundus imaging systems including a fundus imaging apparatus such as a retinal camera, an optical coherence tomography apparatus, an optical scanning ophthalmoscope, and the like, in which a fundus image is associated with a subject through a subject ID (see, for example, Patent Document 3). There are also known medical data retrieval systems, in which patient's name, medical data in the medical records (disease name, etc.), and a fundus image are linked and stored as electronic data (see, for example, Patent Document 4).

Patent Document 1 is the Japanese Unexamined Patent Application Publication No. 2005-279121.

Patent Document 2 is the Japanese Unexamined Patent Application Publication No. 2011-147609.

Patent Document 3 is the Japanese Unexamined Patent Application Publication No. 2002-369801.

Patent Document 4 is the Japanese Unexamined Patent Application Publication No. Hei 06-110947.

SUMMARY OF THE INVENTION

Problems to be Solved by the Invention

Meanwhile, recently, there is a demand for a portable (movable) fundus imaging apparatus to facilitate mass screening, self-examination, and the like. Such a fundus imaging apparatus is desirably small and light.

However, taking a clear image of the fundus requires the alignment of the apparatus body with respect to the subject's eye. The taking a clear image of the fundus also requires focus adjustment with respect to the subject's eye (focusing).

To meet such a demand, as with a common stationary fundus imaging apparatus, a dedicated optical system may be provided to project an alignment indicator and a focus indicator, and receive light. However, such a dedicated optical system increases the size and the complexity of the apparatus, and therefore is not suitable for a portable apparatus that is required to be small, light, and compact.

Besides, if a non-portable (stationary, etc.) fundus imaging apparatus is provided with a dedicated optical system for projecting an alignment indicator, a focus indicator, and a fixation target, which complicates the optical system and a structure to drive it.

The alignment may be performed without the projection of indicators by referring to the brightness of an image at the time of fundus observation or the like. However, this requires skill and is not easy.

The present invention is directed at solving the above problems, and the object is to provide a fundus imaging apparatus capable of performing alignment and focusing without a dedicated optical system for projecting indicators of alignment and focusing.

Means of Solving the Problems

In general, according to one embodiment, a fundus imaging apparatus includes a scanning optical system, a control circuit, and an image forming unit. The scanning optical system scans a fundus of a subject's eye with light from a light source, and receives return light from the fundus by a light receiver. The control circuit controls the scanning optical system such that a scanning locus is formed by the light in the fundus. The image forming unit forms an image of the fundus based on a light receiving signal from the light receiver and a position of the scanning locus. The control circuit is capable of performing an alignment mode, in which the control circuit controls the scanning optical system to project an alignment indicator for aligning the scanning optical system with the subject's eye on the fundus based on the light from the light source.

Effects of the Invention

According to the present invention, alignment and focusing can be performed without a dedicated optical system for projecting indicators of alignment and focusing.

BRIEF DESCRIPTION OF THE DRAWINGS

FIG. 44 is a schematic diagram illustrating an example of the configuration of a fundus imaging system according to an embodiment.

FIRST EMBODIMENT (Overview of the Appearance Configuration of the Optical Scanning Ophthalmoscope)

Figure 1:
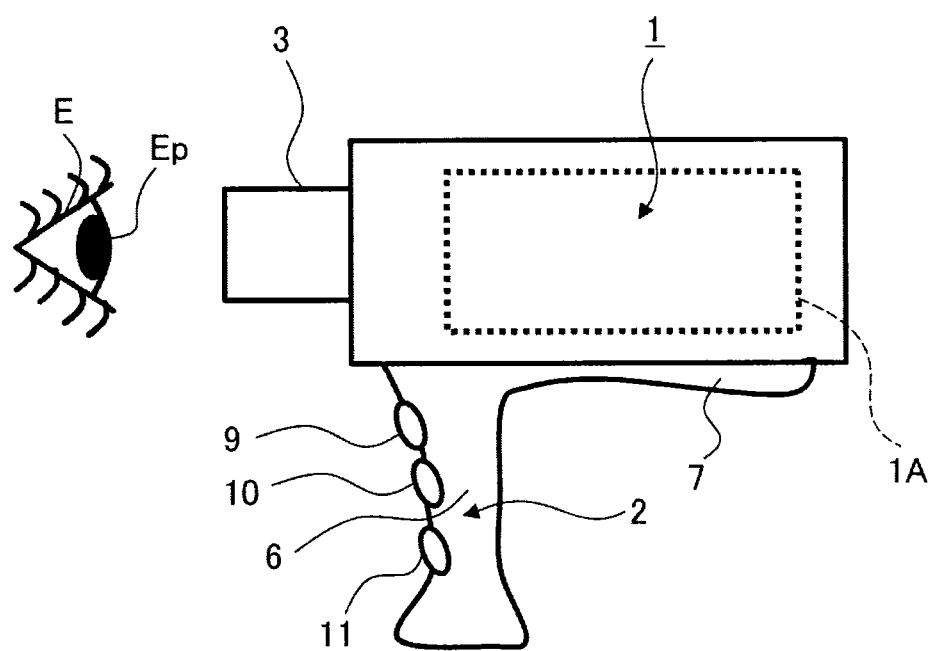
FIG. 1 is a schematic diagram illustrating an example of the configuration of a fundus imaging apparatus according to an embodiment.

FIGS. 1 to 4 are diagrams illustrating a portable (movable) optical scanning ophthalmoscope as a fundus imaging apparatus according to an embodiment. In FIG. 1, reference numeral 1 denotes an optical scanning ophthalmoscope body as the main body of the apparatus, and reference numeral 2 denotes a handle.

Figure 2:
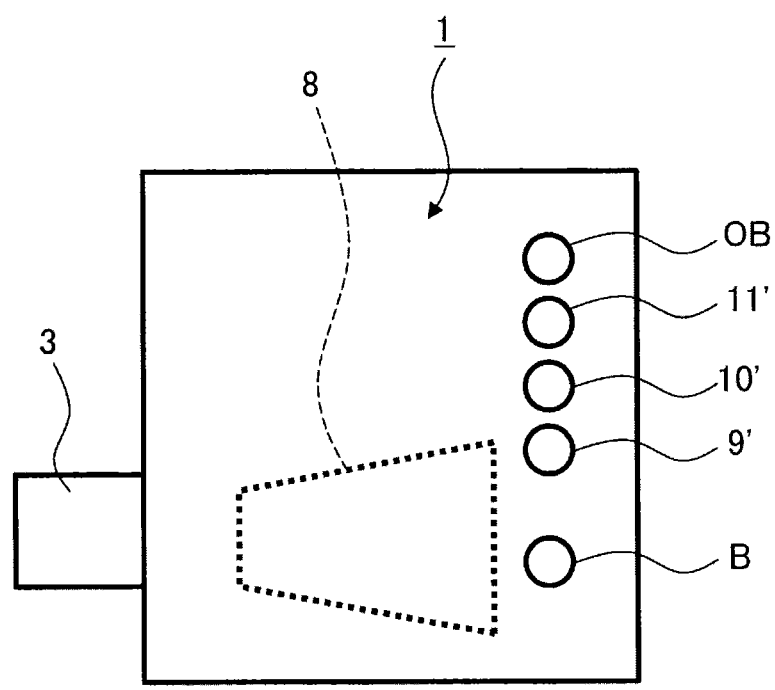
FIG. 2 is a schematic diagram illustrating an example of the configuration of the fundus imaging apparatus according to the embodiment.
Figure 3:
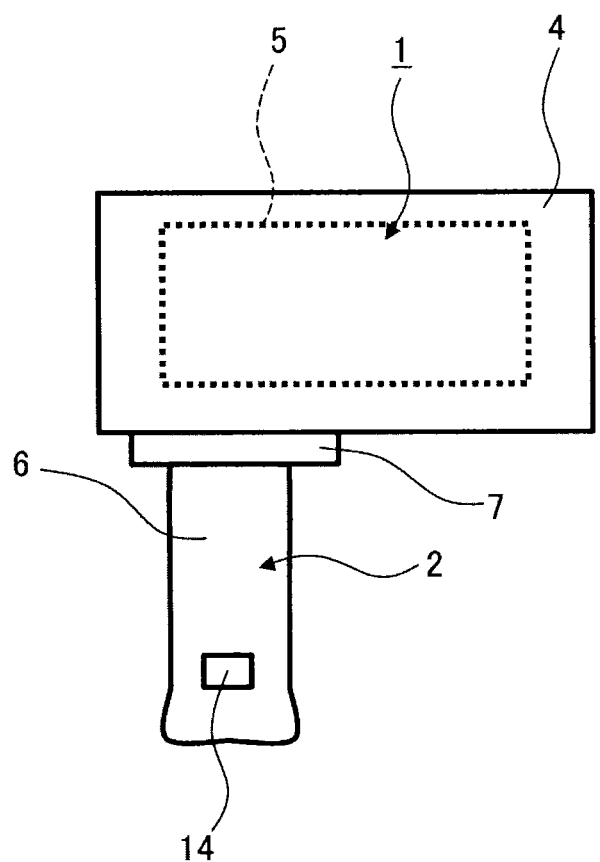
FIG. 3 is a schematic diagram illustrating an example of the configuration of the fundus imaging apparatus according to the embodiment.

As illustrated in FIGS. 1 and 2, an eyepiece tube 3 is located on the front side of the optical scanning ophthalmoscope body 1 (the side facing a subject). As illustrated in FIG. 3, a transparent plate 4 is located on the back side of the optical scanning ophthalmoscope body 1 (the side facing an examiner). The examiner can view a liquid crystal display (LCD) screen 5 of a monitor (described later) through the transparent plate 4.

The optical scanning ophthalmoscope body 1 is provided therein with a laser scanning optical system, a control circuit for controlling the laser scanning optical system, a fundus image forming unit (image forming unit), a lighting control circuit, a monitor, a power supply, and other drive mechanisms necessary for fundus observation imaging. As illustrated in FIG. 2, a power button B for power on/off is arranged on the upper surface of the optical scanning ophthalmoscope body 1.

As illustrated in FIG. 2, the eyepiece tube 3 of this embodiment is located on the left side as viewed from the side facing the examiner. The handle 2 is provided with a grip 6 and an attaching/detaching protrusion 7. A trapezoidal shaped recess 8 illustrated by the dotted line in FIG. 2 is located in a position corresponding to the position of the eyepiece tube 3 in the bottom surface of the optical scanning ophthalmoscope body 1.

The attaching/detaching protrusion 7 has a shape corresponding to the shape of the recess 8 and is fitted in the recess 8. Any one of the attaching/detaching protrusion 7 and the recess 8 is provided with a magnet member (not illustrated).

The other of the attaching/detaching protrusion 7 and the recess 8 is provided with a magnetic member that acts on the attractive force of the magnet member. In this embodiment, the handle 2 is attached to/detached from the optical scanning ophthalmoscope body 1 by the attractive force of the magnet member; however, this is not so limited.

Figure 4:
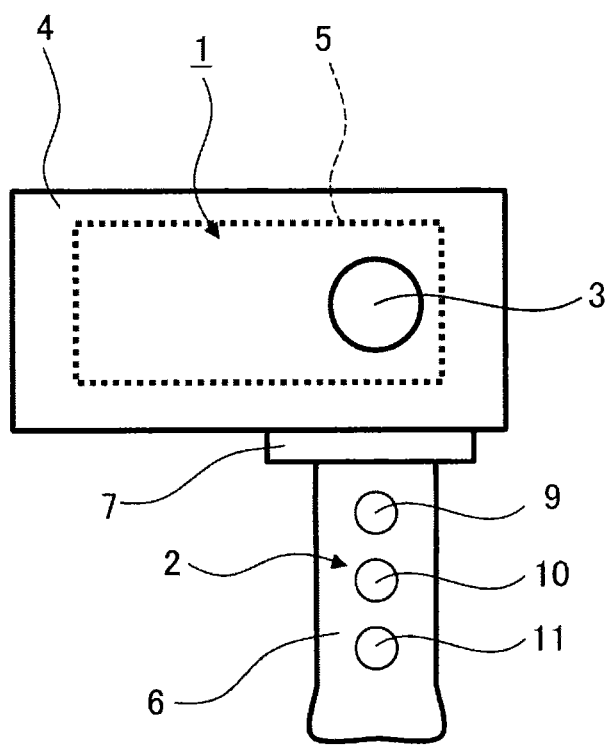
FIG. 4 is a schematic diagram illustrating an example of the configuration of the fundus imaging apparatus according to the embodiment.

As illustrated in FIG. 4, the grip 6 of the handle 2 is provided with a photographing button 9, an alignment button 10, and a focus button 11 (their functions are described later).

Figure 5:
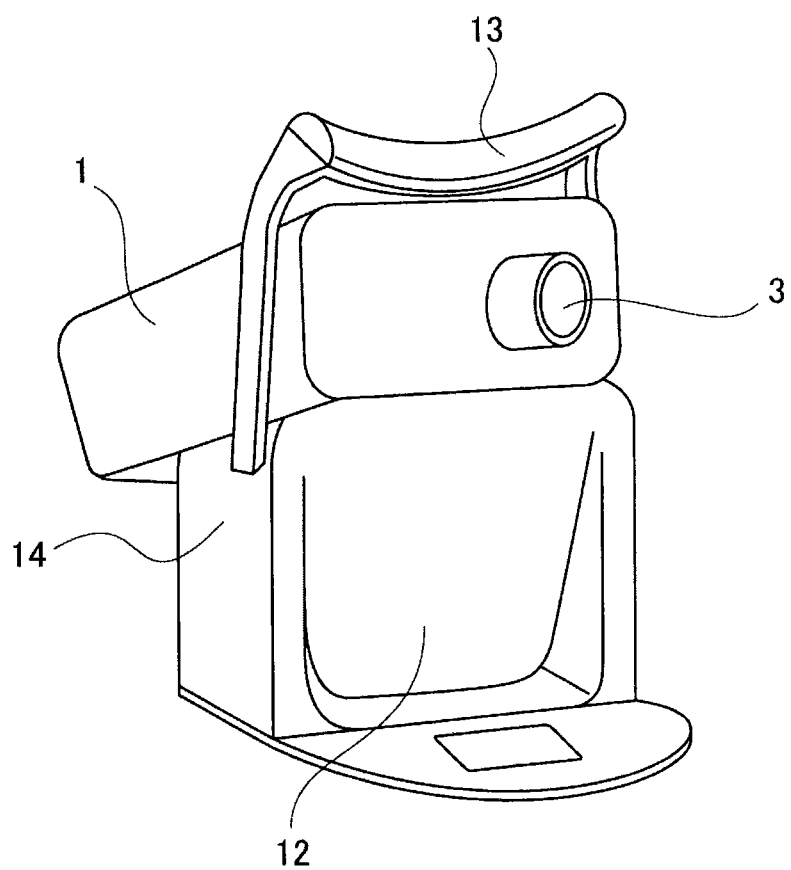
FIG. 5 is a schematic diagram illustrating an example of the configuration of the fundus imaging apparatus according to the embodiment.

As illustrated in FIG. 5, the optical scanning ophthalmoscope of this embodiment can be used in a state of being mounted on a support 12. A forehead pad 13 is provided on the top of the support 12. An engaging protrusion (not illustrated) is formed in an inclined portion 14 of the support 12. When the engaging protrusion is fitted in the recess 8, the optical scanning ophthalmoscope body 1 is supported by the support 12 and is fixed.

Arranged on the top surface of the optical scanning ophthalmoscope body 1 are a photographing button 9', an alignment button 10', and a focus button 11'. Operations on these buttons 9' to 11' are effective when the optical scanning ophthalmoscope body 1 is mounted on the support 12. The photographing button 9', the alignment button 10', and the focus button 11' are enabled/disabled via, for example, a detection switch (not illustrated) provided on the support 12.

Note that the photographing button 9', the alignment button 10', and the focus button 11' may be enabled even when the optical scanning ophthalmoscope body 1 with the handle 2 being removed is used without being mounted on the support 12.

Figure 6:
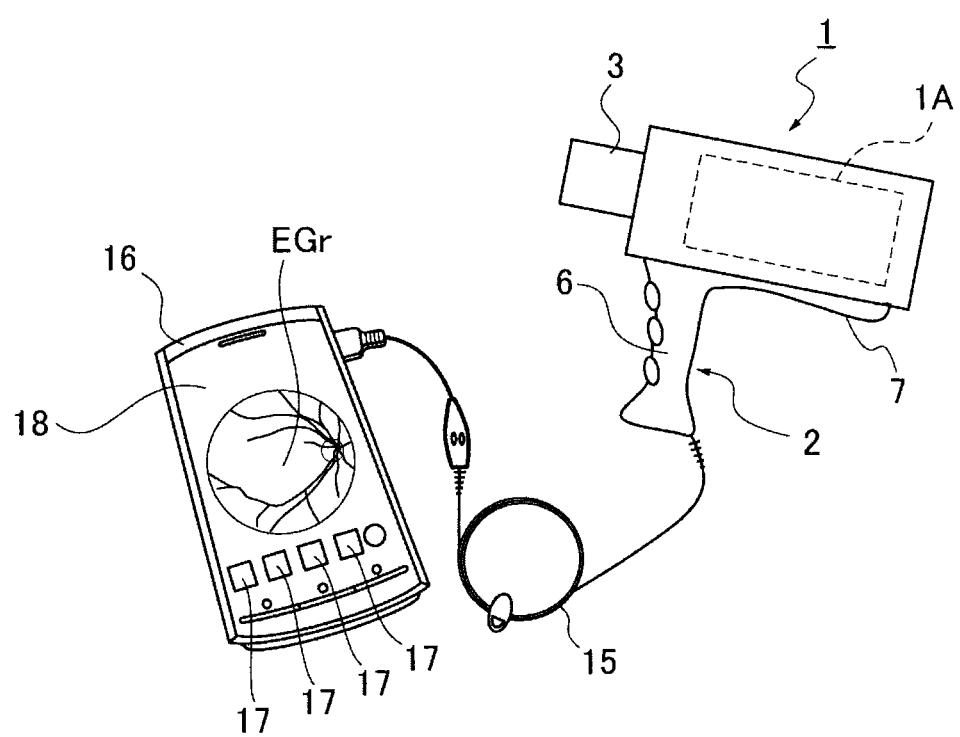
FIG. 6 is a schematic diagram illustrating an example of the usage of the fundus imaging apparatus according to the embodiment.

An attachment plug 14 (USB) is arranged on the bottom of the grip 6 for connecting a portable information device such as smartphone, tablet terminal, personal digital assistant (PDA). The attachment plug 14 is connected to a portable information device 16 illustrated in FIG. 6 via a cord 15. The portable information device 16 has a plurality of operation buttons 17. Here, while the operation buttons 17 are used as alternatives to the photographing button 9, the alignment button 10, and the focus button 11, this is not so limited.

While, in this embodiment, a fundus image EGr is displayed on a display screen 18 of the portable information device 16, this is not so limited. For example, the fundus image EGr may be stored in an built-in memory (described later), and output therefrom in response to operation on an output button OB as illustrated in FIG. 2.

In the following, a description is given of the scanning optical system and the control circuit in the portable optical scanning ophthalmoscope. However, this embodiment is applicable to the optical scanning ophthalmoscope that can be used as a portable device as well as a stationary device, and the stationary optical scanning ophthalmoscope.

Besides, in this embodiment, the fundus image EGr is sequentially stored in the built-in memory. However, the fundus image EGr may be sent to a medical institution via a wired telephone line or a wireless telephone line.
(Overview of the Scanning Optical System and the Control Circuit of the Optical Scanning Ophthalmoscope)

Figure 7:
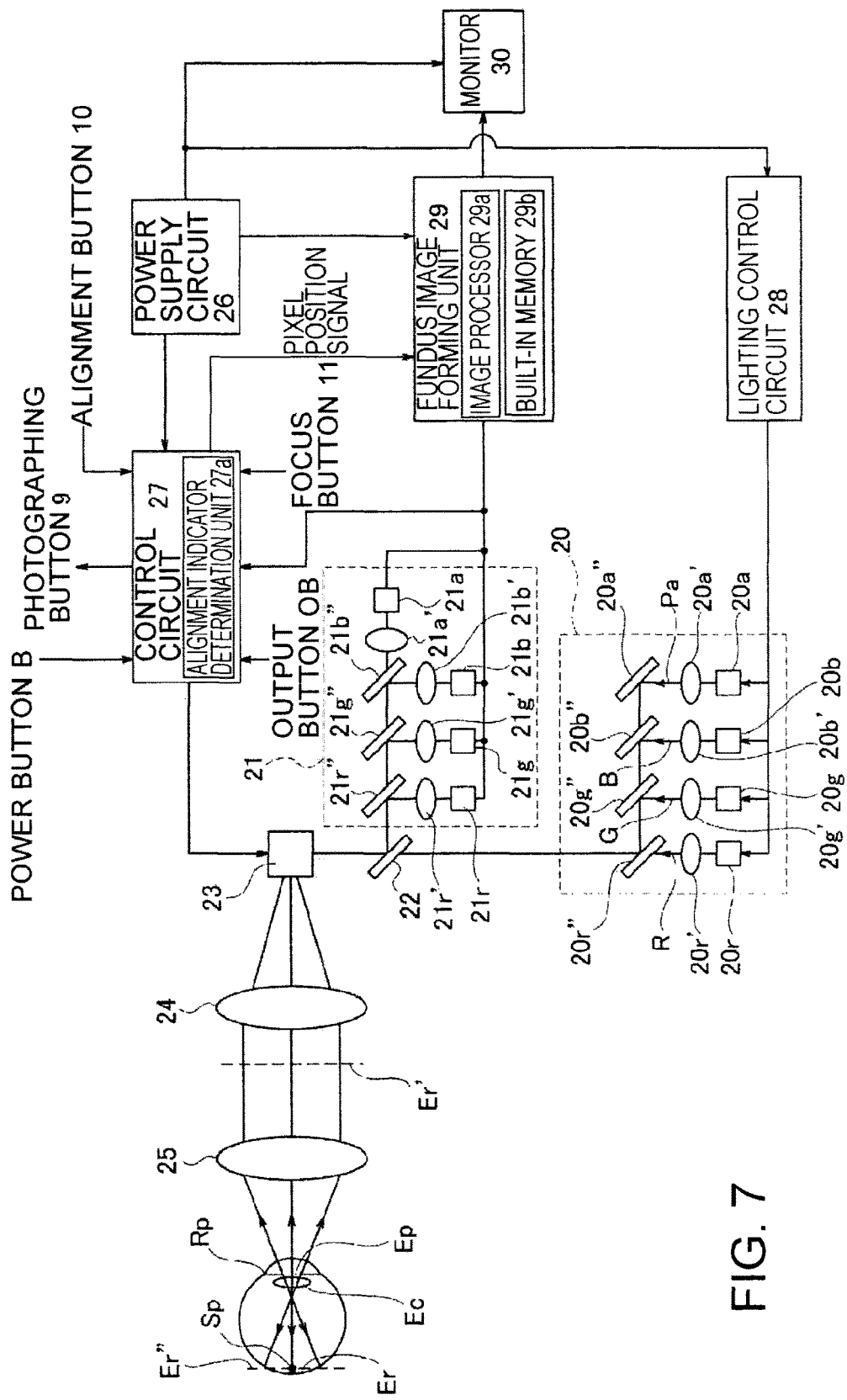
FIG. 7 is a schematic diagram illustrating an example of the configuration of the fundus imaging apparatus according to the embodiment.

FIG. 7 is a block diagram illustrating a scanning optical system and a controller of the optical scanning ophthalmoscope according to the embodiment. Reference numeral 20 denotes an illumination light source that emits illumination light. Reference numeral 21 denotes a light receiver. The illumination light source 20 includes an infrared light source 20a that emits infrared light, a blue light source 20b that generates B light (blue light), a green light source 20g that generates G light (green light), and a red light source 20r that generates R light (red light). As each of these light sources, a light source having a high spatial coherence is used. Examples of such light source include a semiconductor laser (including wavelength tunable laser, super luminescent diode, etc.), a solid-state laser, a gas laser, a device having a configuration in which light emitted from such lasers is combined on an optical fiber, and a fiber laser.

The infrared light Pa emitted from the infrared light source 20a is collected by a condenser lens 20a' and is guided to a reflecting mirror 20a". The blue light B emitted from the blue light source 20b is collected by a condenser lens 20b' and is guided to a dichroic mirror 20b". The green light G emitted from the green light source 20g is collected by a condenser lens 20g' and is guided to a dichroic mirror 20g". The red light R emitted from the red light source 20r is collected by a condenser lens 20r' and is guided to a dichroic mirror 20r".

The dichroic mirror 20b" transmits the infrared light Pa therethrough, and reflects the blue light B. The dichroic mirror 20g" transmits the infrared light Pa and the blue light B therethrough, and reflects the green light G. The dichroic mirror 20r" transmits the red light R therethrough, and reflects the green light G, the blue light B, and the infrared light Pa.

The optical paths of the infrared light Pa, the blue light B, the green light G, and the red light R are combined by the reflecting mirror 20a", the dichroic mirrors 20b", 20g", and 20r". In addition, these light are guided to a beam splitter 22 and pass therethrough, and are guided to a MEMS mirror 23. The MEMS mirror 23 functions as a two-axis optical scanner. In the embodiment, although the MEMS mirror is employed as the two-axis optical scanner, it is not so limited. For example, a combination of two uniaxial mirror scanners such as a galvano-mirror optical scanner, a polygon mirror optical scanner or the like may constitute a two-axis optical scanner. In this case, a relay lens optical system may be provided between the two uniaxial mirror scanners included in the two-axis optical scanner.

The infrared light Pa, the blue light B, the green light G, and the red light R are two-dimensionally deflected by the MEMS mirror 23. In addition, these light are guided to a relay lens 24, and are focused in the air as a light spot in a plane Er' conjugate to the fundus Er of the subject's eye E.

The light aerially focused in the conjugate plane Er' passes through an objective lens 25 as a focusing lens, and is guided into the eye through the pupil Ep and the crystalline lens Ec of the subject's eye E. The light is then focused as a light spot Sp in the conjugate plane Er" of the fundus Er conjugate to the conjugate plane Er'.

The objective lens 25 is arranged on the eyepiece tube 3, and is manually moved in the axial direction. When an annular ring member (not illustrated) of the eyepiece tube 3 is rotated according to the refractive power of the subject's eye E, the objective lens 25 is moved in the optical axis direction. As a result, the conjugate plane Er" matches the fundus Er, and thus a sharp light spot Sp is formed on the fundus Er.

Figure 8:
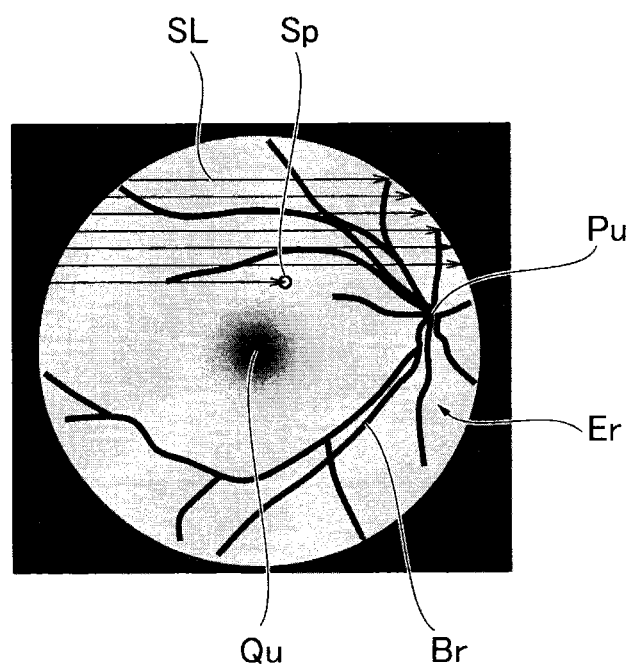
FIG. 8 is a schematic diagram for explaining an example of the operation of the fundus imaging apparatus according to the embodiment.

As illustrated in FIG. 8, the fundus Er is two-dimensionally scanned by the operation of the MEMS mirror 23. In FIG. 8, reference symbol SL denotes the scanning locus of the light spot Sp, reference symbol Br denotes a blood vessel, reference symbol Pu denotes an optic papilla (optic disc), and reference symbol Qu denotes a macula.

A light spot reflected from the fundus Er is led to the objective lens 25 through the crystalline lens Ec and the pupil Ep, and is once aerially focused in the conjugate plane Er'. The light is then collimated by the relay lens 24, passes through the MEMS mirror 23, and is guided to the beam splitter 22. The reflect light spot reflected by the beam splitter 22 is guided to the light receiver 21. Here, the light spot reflected from the fundus Er is light (return light) returning from the position of the scanning light spot or around the position. The light includes at least one of, for example, regularly reflected light of the scanning light spot, the scattered light of the scanning light spot, fluorescence excited by the scanning light spot and its scattered light.

The light receiver 21 includes dichroic mirrors 21$r''$, 21$g''$, and 21$b''$. The dichroic mirror 21$r''$ reflects the red light R, and transmits the green light G, the blue light B, and the infrared light Pa therethrough. The dichroic mirror 21$g''$ reflects the green light G, and transmits the blue light B and the infrared light Pa therethrough. The dichroic mirror 21$b''$ reflects the blue light B, and transmits the infrared light Pa therethrough.

An imaging lens 21$r'$ is located in a direction in which the dichroic mirror 21$r''$ reflects the light. The red light R forms an image on a PD sensor 21$r$ as an image-receiving element by the imaging lens 21C.

An imaging lens 21$g'$ is located in a direction in which the dichroic mirror 21$g''$ reflects the light. The green light G forms an image on a PD sensor 21$g$ as an image-receiving element by the imaging lens 21$g'$.

An imaging lens 21$b'$ is located in a direction in which the dichroic mirror 21$b''$ reflects the light. The blue light B forms an image on a PD sensor 21$b$ as an image-receiving element by the imaging lens 21$b'$.

An imaging lens 21$a'$ is located in the transmission direction of the dichroic mirror 21$b''$. The infrared light Pa forms an image on a PD sensor 21$a$ as an image-receiving element by the imaging lens 21$a'$.

Light receiving signals from the PD sensors 21$a$, 21$b$, 21$g$ and 21$r$ are fed to a fundus image forming unit (described later). Incidentally, the PD sensor 21$a$ has sensitivity to an infrared region, the PD sensor 21$b$ has sensitivity to a blue wavelength region, the PD sensor 21$g$ has sensitivity to a green wavelength region, and the PD sensor 21$r$ has sensitivity to a red wavelength region.

(One Example of the Internal Structure of the Optical Scanning Ophthalmoscope Body 1)

The optical scanning ophthalmoscope body 1 of this embodiment includes therein a movable casing 1A illustrated by a broken line in FIG. 1 and a drive mechanism (not illustrated) for moving the movable casing 1A in the longitudinal, vertical, and horizontal directions. The movable casing 1A and the drive mechanism correspond to a "drive unit".

The movable casing 1A contains therein the illumination light source 20, the light receiver 21, the relay lens 24, the MEMS mirror 23, and the beam splitter 22. These optical systems and the eyepiece tube 3 move integrally with the movable casing 1A.

As illustrated in FIG. 7, the optical scanning ophthalmoscope body 1 includes therein a power supply circuit 26, a control circuit 27, a lighting control circuit 28, a fundus image forming unit 29, and a monitor 30. For example, the power supply circuit 26 is of a type that allows the battery to be replaced or charged.

The power supply circuit 26 supplies power to the control circuit 27, the fundus image forming unit 29, the lighting control circuit 28, and the like. The control circuit 27 is provided with a program for controlling the illumination light source 20, a program for controlling the MEMS mirror 23, and a program for controlling the fundus image forming unit 29.

The program for controlling the illumination light source 20 and the program for controlling the MEMS mirror 23 are provided according to various operation modes as, for example, follows: alignment adjustment mode for performing the alignment of the apparatus body with respect to the subject's eye E; focus adjustment mode for performing focusing for the fundus Er; fundus observation mode; and photographing mode.

In response to operation on the power button B, each circuit is activated. Since alignment adjustment and focus adjustment are not directly related to this embodiment, it is assumed that these adjustments have already been completed. In the following, the observation mode and the photographing mode are described, and then the association between a fundus image and personal information is described.

(Observation Mode)

When the examiner operates the power button B, the optical scanning ophthalmoscope body 1 automatically enters in personal information acquisition mode, and then switches to the observation mode. The personal information acquisition mode is described later, and the observation mode is described first. In the observation mode, the lighting control circuit 28 turns on the infrared light source 20$a$. With this, as illustrated in FIG. 8, the light spot Sp, which is infrared light, is formed on the fundus Er.

According to a program for controlling this, the MEMS mirror 23 is driven, for example, as illustrated in FIG. 8, to draw a plurality of scanning loci SL directed from left to right in order from the top. Thereby, a predetermined area of the fundus Er is scanned with the light spot Sp.

The reflected light of the light spot Sp from the fundus Er is received by the PD sensor 21$a$ for receiving infrared light. The fundus image forming unit 29 receives a light receiving signal from the PD sensor 21$a$. The fundus image forming unit 29 includes an image processor 29$a$ and a built-in memory 29$b$.

According to a program for controlling the MEMS mirror 23, the image processor 29$a$ receives a pixel position signal corresponding to the scanning position of the light spot Sp (horizontal scanning locus position, vertical scanning locus position).

Figure 9:
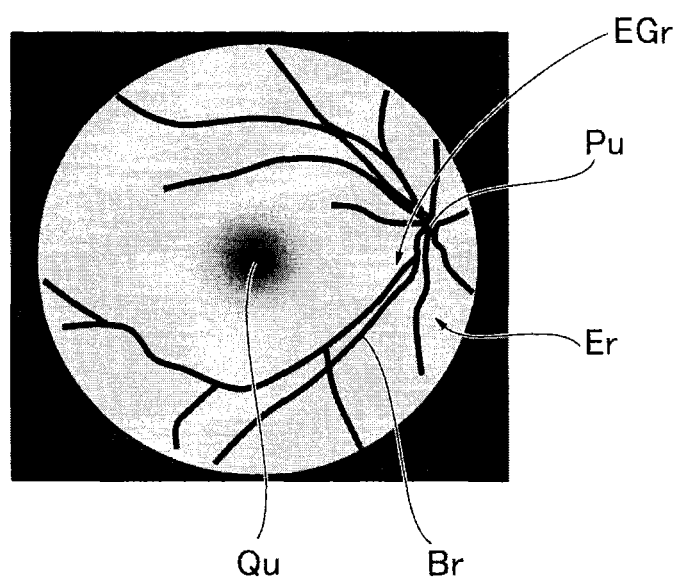
FIG. 9 is a schematic diagram for explaining an example of the operation of the fundus imaging apparatus according to the embodiment.

The image processor 29$a$ forms a fundus image for observation based on the pixel position signal and a light receiving signal corresponding to the pixel position signal. The image processor 29$a$ outputs an image signal of the fundus image to the monitor 30. Thus, the fundus image EGr is displayed on the LCD screen 5 of the monitor 30 (see FIG. 9).

The examiner operates the photographing button 9 while observing the fundus image EGr. In response to this operation, the operation mode of the optical scanning ophthalmoscope switches to the photographing mode.

(Photographing Mode)

In the photographing mode, the lighting control circuit 28 turns on the blue light source 20$b$, the green light source 20$g$, and the red light source 20$r$ at the same time. The lighting time is set to, for example, 100 milliseconds. While the blue light source 20b, the green light source 20g, and the red light source 20r are lighting, the MEMS mirror 23 is driven to draw the same scanning loci SL as the scanning locus loci on the occasion of forming the fundus image for observation.

As a result, the fundus Er is scanned with a white light spot Sp, which is visible light, in the same manner as in the observation mode. The reflected light of the white light spot Sp is received by the PD sensors 21b, 21g and 21r. The fundus image forming unit 29 receives light receiving signals from the PD sensors 21b, 21g and 21r.

The fundus image forming unit 29 forms a color fundus image EGr based on the light receiving signals from the PD sensors 21b, 21g and 21r. The color fundus image EGr is stored in the built-in memory 29b.

The optical scanning ophthalmoscope body 1 may be provided with a play button (not illustrated). In response to operation on the play button, the color fundus image EGr may be displayed on the LCD screen 5. Further, in response to operation on the play button, the color fundus image EGr acquired may be automatically sent to a medical institution. In this embodiment, upon completion of photographing, the operation mode of the optical scanning ophthalmoscope automatically switches to the observation mode.

(Alignment Mode)

First, a description is given of the reason why alignment is required with respect to the subject's eye E.

Figure 10:
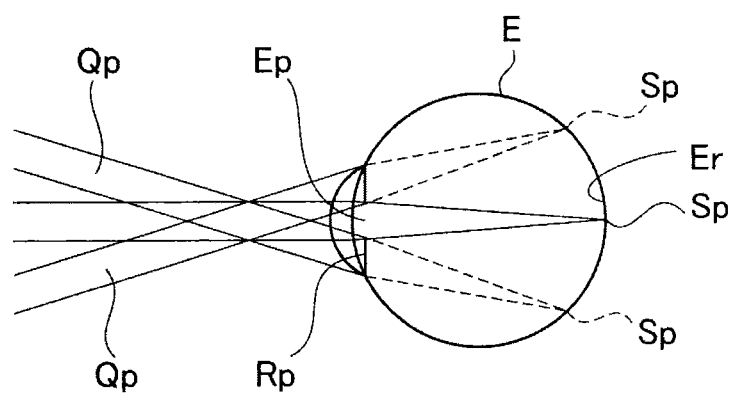
FIG. 10 is a schematic diagram for explaining an example of the operation of the fundus imaging apparatus according to the embodiment.
Figure 11:
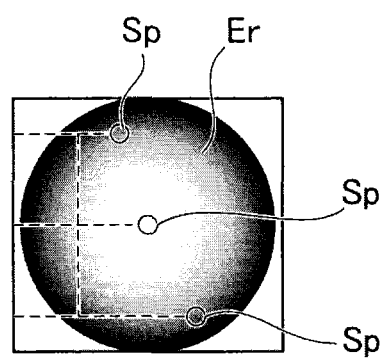
FIG. 11 is a schematic diagram for explaining an example of the operation of the fundus imaging apparatus according to the embodiment.

As schematically illustrated in FIG. 10, if the apparatus body (optical system) is misaligned with respect to the subject's eye E in the optical axis direction, among illumination light fluxes from the light source 20, oblique light fluxes Qp that are obliquely incident into the anterior segment from the periphery are symmetrically blocked by the iris Rp. With this, the amount of light that reaches the periphery of the fundus Er is reduced. As a result, as schematically illustrated in FIG. 11, the amount of light spot Sp formed in the periphery of the fundus Er is reduced. Thus, the peripheral region of the fundus Er is darkly illuminated, while the central region is brightly illuminated. Incidentally, broken lines in FIG. 10 indicate light fluxes blocked by the iris Rp.

Figure 12:
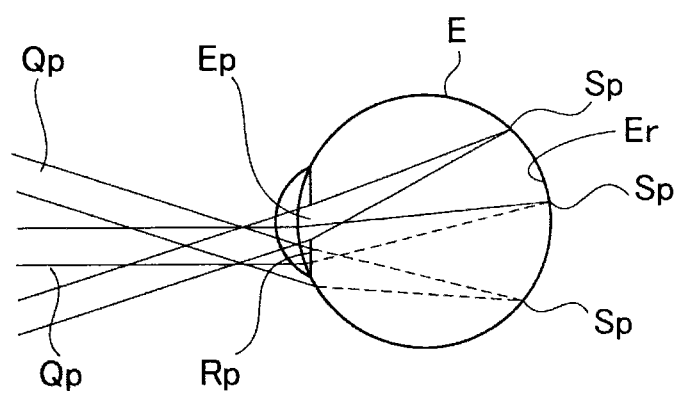
FIG. 12 is a schematic diagram for explaining an example of the operation of the fundus imaging apparatus according to the embodiment.

As schematically illustrated in FIG. 12, when alignment is not achieved with respect to the subject's eye E in a direction perpendicular to the optical axis of the apparatus body, for example, among the illumination light fluxes from the light source 20, one of the oblique light fluxes Qp that are obliquely incident into the anterior segment from the periphery is blocked by the iris Rp, while the other passes through the pupil Ep.

Figure 13:
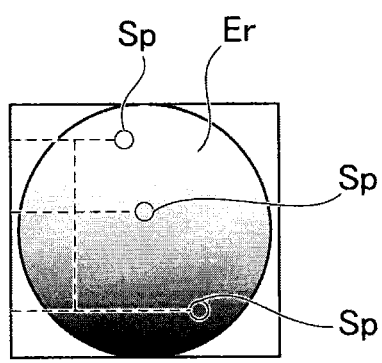
FIG. 13 is a schematic diagram for explaining an example of the operation of the fundus imaging apparatus according to the embodiment.

As a result, the amount of light spot Sp formed on one side of the peripheral region of the fundus Er is reduced, while the amount of light spot Sp is not reduced on the other side. Thus, as schematically illustrated in FIG. 13, one side of the peripheral region of the fundus Er is darkly illuminated, while the other side is brightly illuminated. This causes unevenness in brightness in the illumination region of the fundus Er. Incidentally, broken lines in FIG. 12 indicate light fluxes blocked by the iris Rp.

Figure 14:
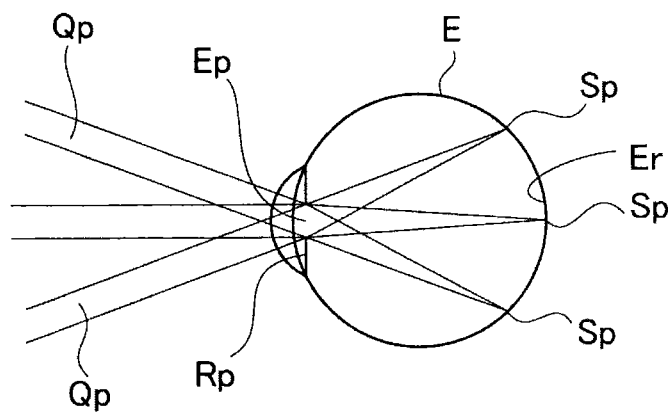
FIG. 14 is a schematic diagram for explaining an example of the operation of the fundus imaging apparatus according to the embodiment.
Figure 15:
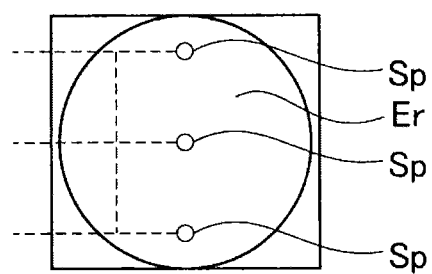
FIG. 15 is a schematic diagram for explaining an example of the operation of the fundus imaging apparatus according to the embodiment.

On the other hand, when the apparatus body is aligned properly with respect to the subject's eye E in both the optical axis direction and the direction perpendicular thereto, as illustrated in FIG. 14, the oblique light fluxes Qp pass through the pupil Ep and are incident symmetrically. Thus, the fundus Er can be illuminated without unevenness in brightness.

When the alignment button 10 is operated, the operation mode of the optical scanning ophthalmoscope body 1 switches to the alignment mode. The control circuit 27 controls the MEMS mirror 23 so that the scanning locus SL of the light spot Sp becomes circular. At the same time, the lighting control circuit 28 turns on the infrared light source 20a. Further, in the alignment mode, the control circuit 27 receives a light receiving signal from the PD sensor 21a at the same time.

Figure 16:
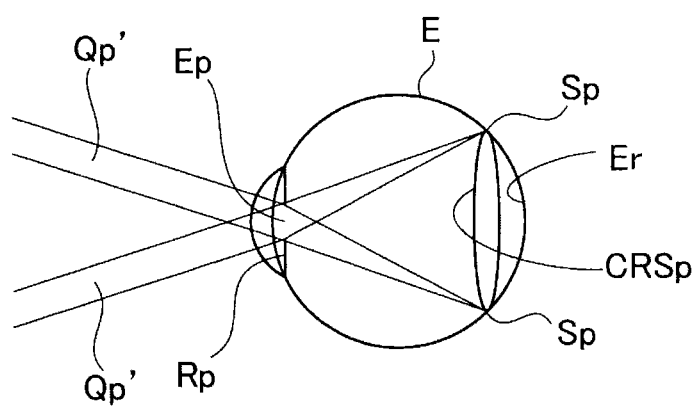
FIG. 16 is a schematic diagram for explaining an example of the operation of the fundus imaging apparatus according to the embodiment.
Figure 17:
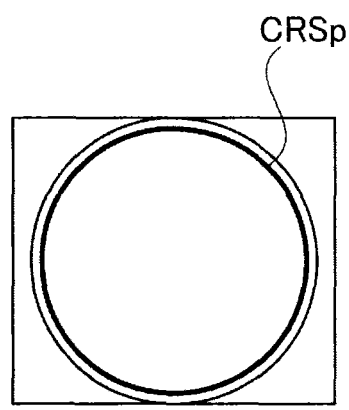
FIG. 17 is a schematic diagram for explaining an example of the operation of the fundus imaging apparatus according to the embodiment.

If the apparatus body is aligned with respect to the subject's eye E, as illustrated in FIG. 16, the oblique light fluxes Qp' that form a circular locus CRSp pass through the pupil Ep. Accordingly, as schematically illustrated in FIG. 17, the circular locus CRSp is formed by the light spot Sp on the fundus Er. The fundus image forming unit 29 forms an image that corresponds to the circular locus CRSp. In addition, an alignment indicator image corresponding to the circular locus CRSp is displayed on the LCD screen 5.

Figure 18:
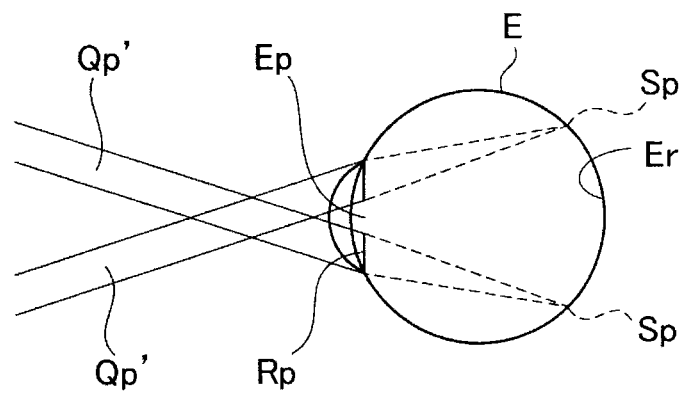
FIG. 18 is a schematic diagram for explaining an example of the operation of the fundus imaging apparatus according to the embodiment.

If the apparatus body is not aligned with respect to the subject's eye E, for example, when the alignment is improper in the optical axis direction, as illustrated in FIG. 18, the oblique light fluxes Qp' forming the circular locus CRSp are blocked by the iris Rp. Accordingly, the circular locus CRSp of the light spot Sp is not formed on the fundus Er, and an alignment indicator image corresponding to the circular locus CRSp is not displayed on the LCD screen 5.

Figure 19:
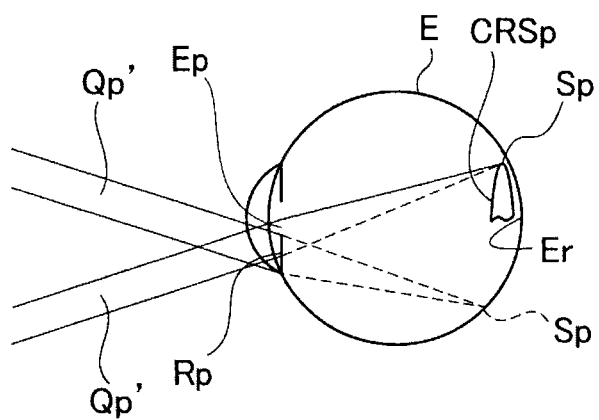
FIG. 19 is a schematic diagram for explaining an example of the operation of the fundus imaging apparatus according to the embodiment.

Further, if the apparatus body is misaligned with respect to the subject's eye E in a direction perpendicular to the optical axis of the apparatus body, as illustrated in FIG. 19, part of the oblique light fluxes Qp' which forms a circular locus CRSp is blocked by the iris Rp. The locus in a shape having lost part of the circular locus CRSp is formed by the light spot Sp on the fundus Er, and an alignment indicator image of this shape is displayed on the LCD screen 5. With the alignment indicator image displayed on the LCD screen 5, the examiner can check whether part of the circular locus CRSp has been lost, whereby the alignment of the apparatus body with respect to the subject's eye E (i.e., whether alignment is proper or not) can be figured out.

In addition, by checking the direction in which an alignment indicator image corresponding to the circular locus CRSp has been partly lost, the examiner can determine the direction to move the apparatus body with respect to the subject's eye E.

An example is described above in which a single circular locus CRSp is used. However, circular loci CRSp formed of multiple concentric rings, a spiral, or the like may also be used as an alignment indicator.

Moreover, by analyzing the state of the circular locus CRSp in the fundus image forming unit 29, it is possible to automatically determine whether alignment is proper or not. In addition, the determination result as to whether alignment is proper or not may also be displayed on the LCD screen 5.

(Modifications of the Alignment Indicator)

FIGS. 20 to 26 are explanatory views illustrating modifications of the alignment indicator. An example is described above in which the scanning locus of the light spot Sp made by the MEMS mirror 23 is changed at the time of observing/photographing the fundus and alignment adjustment.

However, the alignment indicator can be projected by synchronous control on the lighting timing of the infrared light source 20a according to the scanning position of the MEMS mirror 23 with the same scanning method as that in the observing/photographing time.

(Modification 1)

Figure 20:
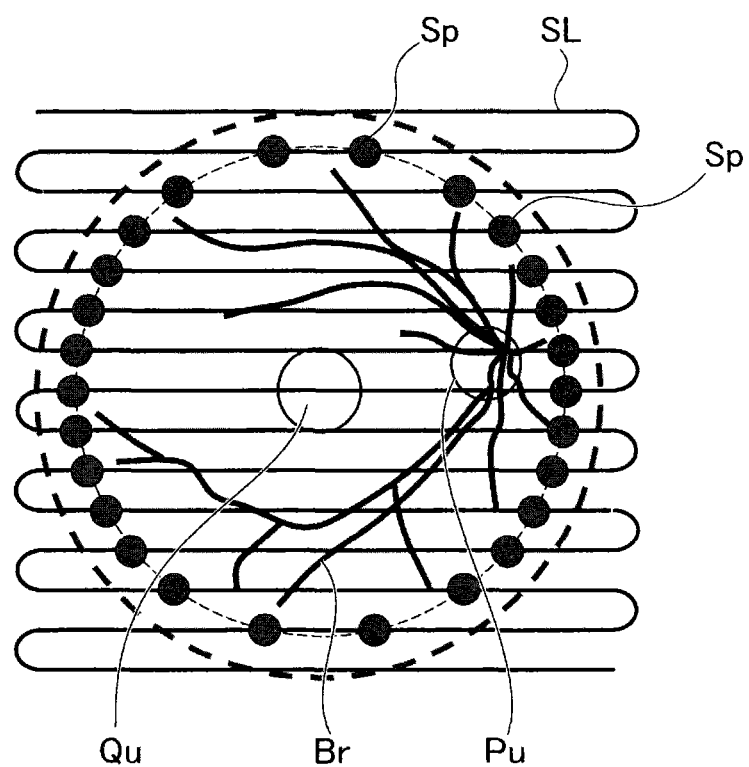
FIG. 20 is a schematic diagram for explaining an example of the operation of the fundus imaging apparatus according to the embodiment.

FIG. 20 illustrates a control to synchronize the scanning position of the MEMS mirror 23 with the lighting timing of the infrared light source 20a such that the light spot Sp draws a circular discontinuous locus on the fundus Er.

Here, the scanning locus SL is formed by reciprocal scanning so as to draw a single stroke.

Besides the configuration in which the scanning position of the MEMS mirror 23 is controlled to be synchronized with on/off of the infrared light source 20a, for example, such configuration as follows may also be employed. First, the infrared light source 20a is constantly turning on. Then, the scanning position of the MEMS mirror 23 is controlled to be synchronized with the output timing of the PD sensor 21a so that the PD sensor 21a sends only a light receiving signal of reflected light from the scanning position corresponding to the alignment indicator to the fundus image forming unit 29.

(Modification 2)

Figure 21:
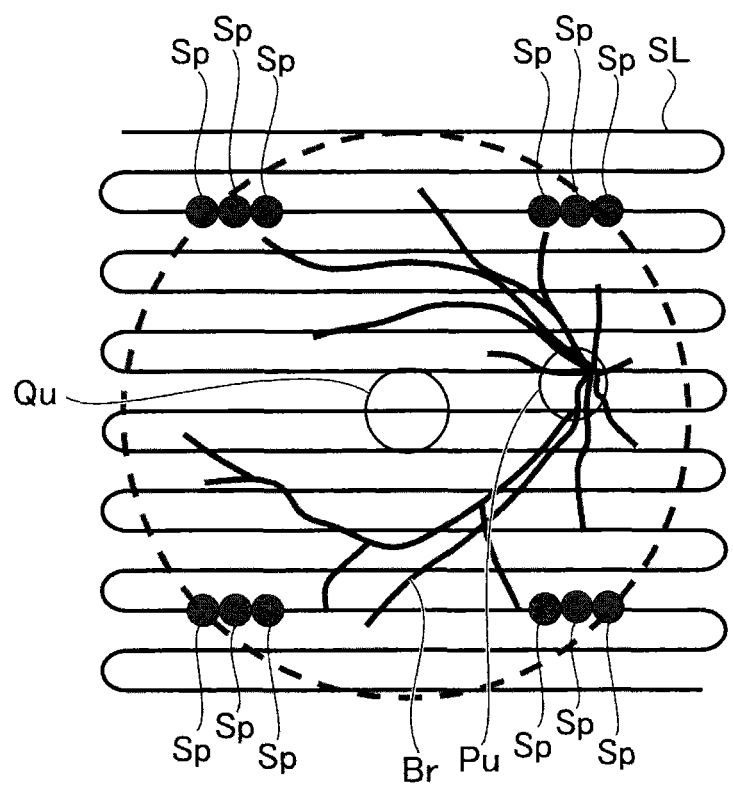
FIG. 21 is a schematic diagram for explaining an example of the operation of the fundus imaging apparatus according to the embodiment.

An example is described above in which an alignment indicator is formed by drawing a circular locus CRSp on the fundus Er. However, as illustrated in FIG. 21, the light spot Sp may be irradiated on the fundus Er to form a plurality of alignment indicators in different positions.

In this modification, when the apparatus body is aligned properly with the subject's eye E, an alignment indicator consisting of a horizontal array of three light spots Sp is formed in each of four corners, i.e., upper left and right corners, lower left and right corners, of the fundus Er.

Figure 22:
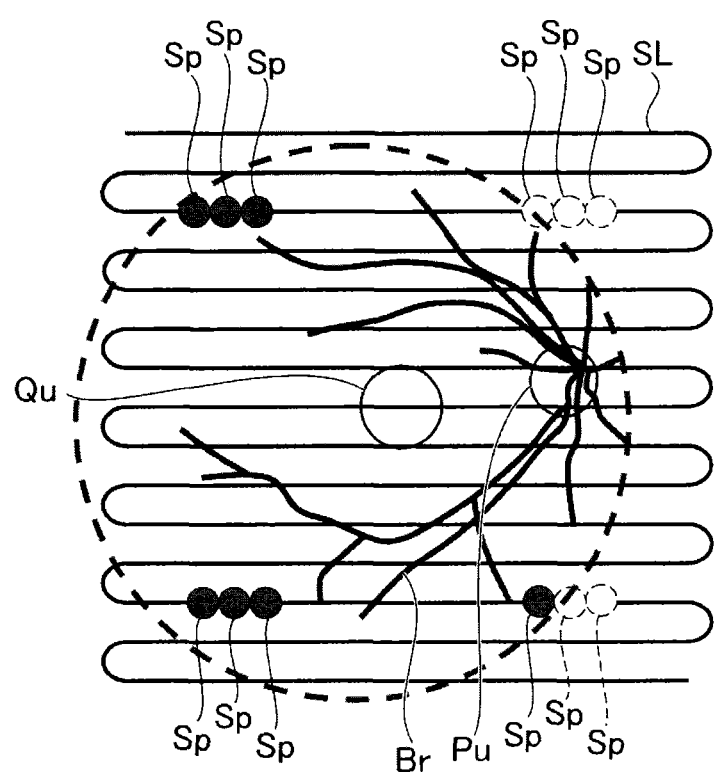
FIG. 22 is a schematic diagram for explaining an example of the operation of the fundus imaging apparatus according to the embodiment.

On the other hand, FIG. 22 illustrates an example when the apparatus body is misaligned with respect to the subject's eye E. In the example of FIG. 22, all three light spots Sp are missing in the upper right corner, and two of three light spots Sp are missing in the lower right corner. The examiner can determine the direction and amount to move the apparatus body with respect to the subject's eye E based on the state of lack of the light spots Sp.

(Modification 3)

Figure 23:
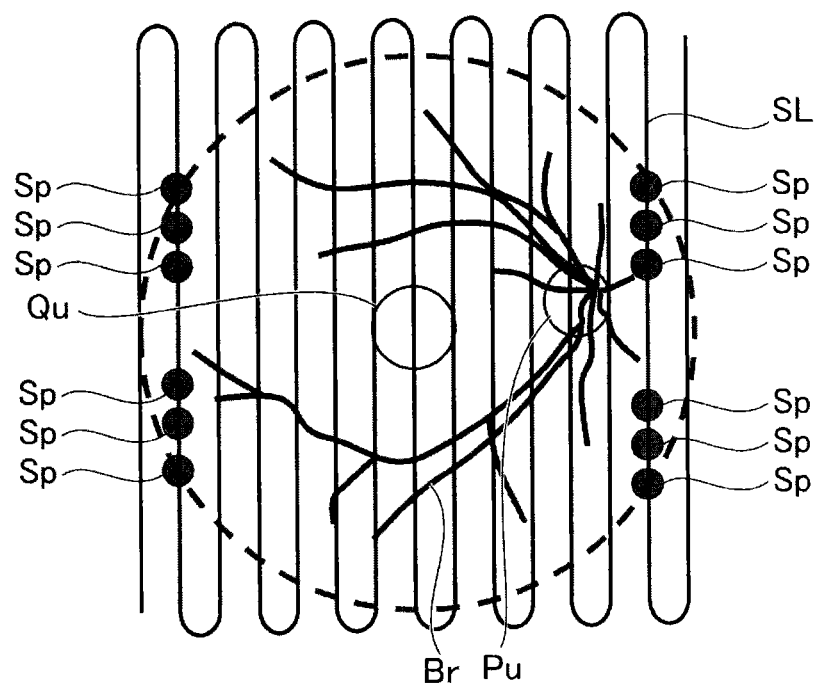
FIG. 23 is a schematic diagram for explaining an example of the operation of the fundus imaging apparatus according to the embodiment.

In the example of FIG. 23, the scanning locus SL is drawn with a single stroke in the vertical direction, and an alignment indicator consisting of a vertical array of three light spots Sp is formed in each of four corners, i.e., upper left and right corners, lower left and right corners, of the fundus Er.

Figure 24:
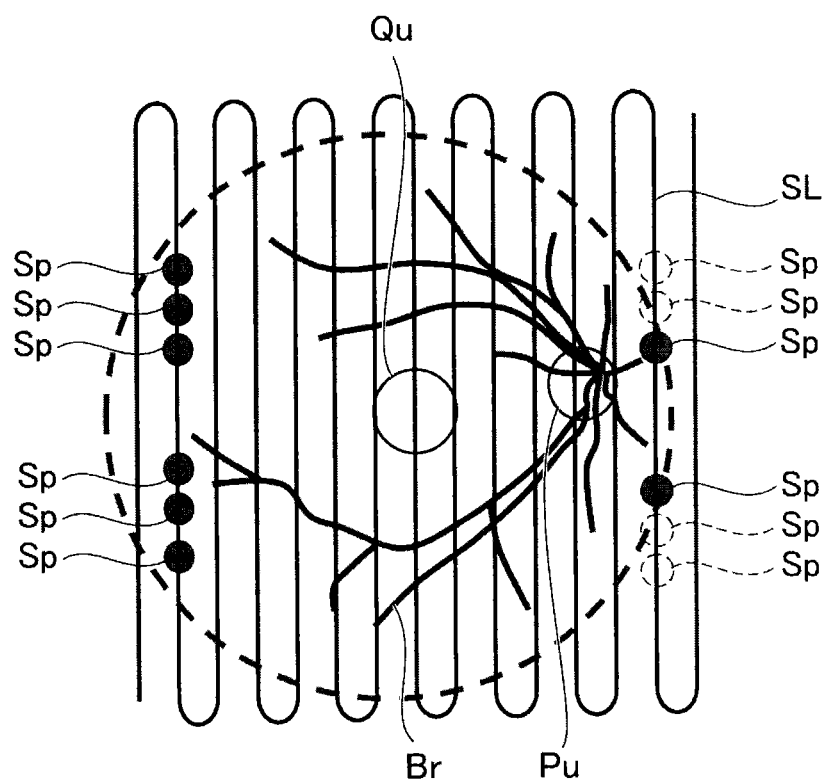
FIG. 24 is a schematic diagram for explaining an example of the operation of the fundus imaging apparatus according to the embodiment.

If the apparatus body is misaligned horizontally with respect to the subject's eye E, for example, as illustrated in FIG. 24, two of three light spots Sp are missing in the upper right corner, and two of three light spots Sp are missing in the lower right corner. The examiner can determine the direction and amount to move the apparatus body with respect to the subject's eye E based on the state of lack of the light spots Sp.

(Modification 4)

Figure 25:
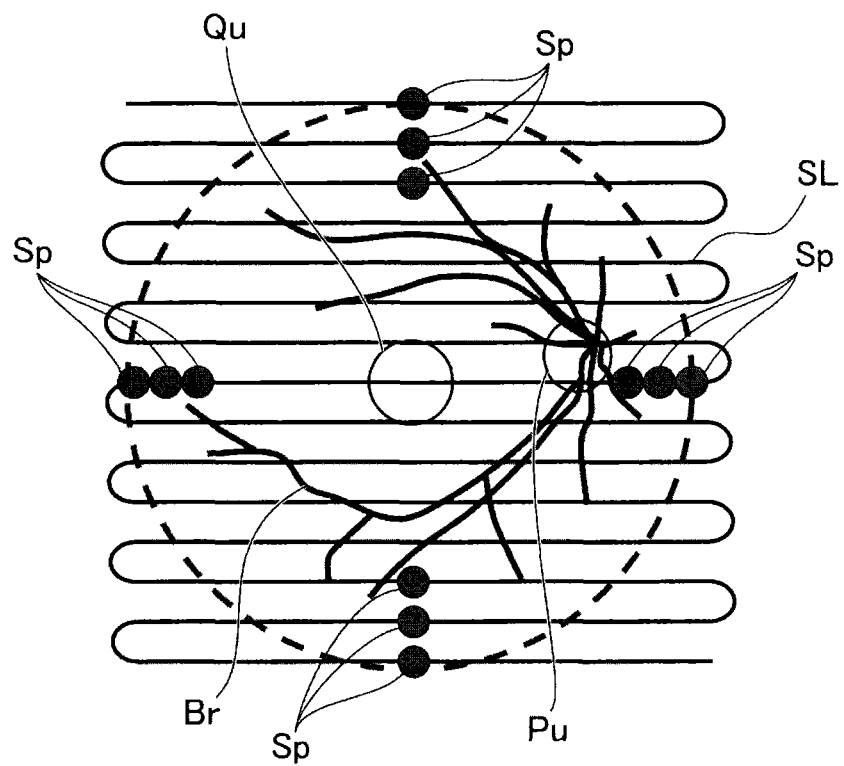
FIG. 25 is a schematic diagram for explaining an example of the operation of the fundus imaging apparatus according to the embodiment.

FIG. 25 illustrates an example in which the scanning locus SL is drawn with a single stroke in the horizontal direction, an alignment indicator consisting of a vertical array of three light spots Sp is formed in the upper center position and the lower center position, and an alignment indicator consisting of a horizontal array of three light spots Sp is formed in the left center position and the right center position. That is, in this modification, alignment indicators are formed in a cross shape on the fundus Er.

Figure 26:
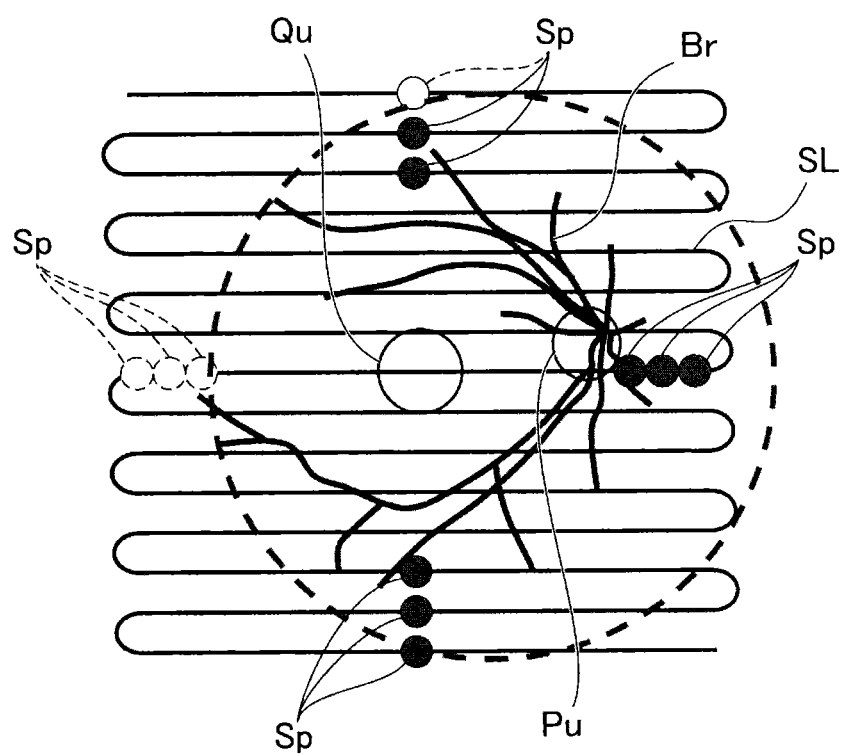
FIG. 26 is a schematic diagram for explaining an example of the operation of the fundus imaging apparatus according to the embodiment.

If the apparatus body is misaligned horizontally with respect to the subject's eye E, for example, as illustrated in FIG. 26, three light spots Sp are missing in the left position. The examiner can determine the direction and amount to move the apparatus body with respect to the subject's eye E based on the state of lack of the light spots Sp.

The control circuit 27 may be provided with an alignment indicator determination unit 27a. The alignment indicator determination unit 27a moves the movable casing 1A in the longitudinal, vertical, and horizontal directions so that the apparatus body is aligned properly with the subject's eye E depending on the state of formation of light spots Sp as alignment indicators.

(Focus Mode)

If the user operates the focus button 11 after the completion of the alignment adjustment of the apparatus body with respect to the subject's eye E, the operation mode of the optical scanning ophthalmoscope body 1 switches to the focus mode. The operation mode may automatically switch to the focus mode triggered by the completion of the alignment adjustment. In this case, the focus button 11 is unnecessary.

Figure 27:
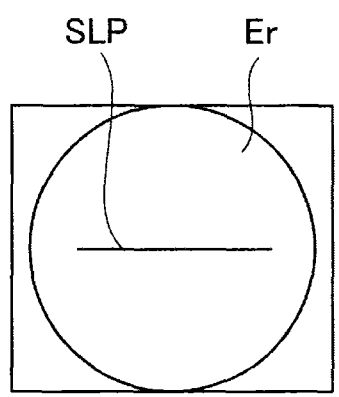
FIG. 27 is a schematic diagram for explaining an example of the operation of the fundus imaging apparatus according to the embodiment.

If the apparatus body is out of focus with respect to the subject's eye E, the fundus image EGr is blurred and is darken as a whole. In this example, as illustrated in FIG. 27, a linear indicator SLP is formed on the fundus Er as a focus indicator.

The control circuit 27 controls the lighting control circuit 28 to form a linear indicator SLP extending in the lateral direction (horizontal direction) in the center of the fundus Er. At this time, the lighting control circuit 28 synchronously controls the MEMS mirror 23 and the lighting of the infrared light source 20a.

Figure 28:
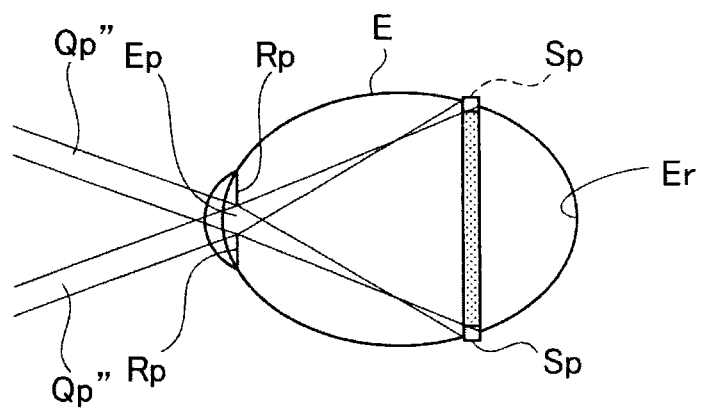
FIG. 28 is a schematic diagram for explaining an example of the operation of the fundus imaging apparatus according to the embodiment.

As illustrated in FIG. 28, the light fluxes Qp" that form the linear indicator SLP pass through the pupil Ep, and are irradiated to the fundus Er. When the light spot Sp is out of focus with respect to the fundus Er, the diameter of the light spot Sp becomes large, and a blurry spot is formed on the fundus Er. Therefore, as the width of the linear indicator SLP increases, the linear indicator SLP becomes blurred.

The fundus image forming unit 29 forms a focus indicator image corresponding to the linear indicator SLP based on a light receiving signal from the PD sensor 21a.

In this embodiment, the focus indicator image is formed in the following manner. The PD sensor 21a detects the amount of light received from the scanning locus position, and cannot detect information on the size of the light spot Sp. However, when the focus is not correct, the amount of light received by the PD sensor 21a is reduced. Therefore, by performing actual measurement in advance, the PD sensor 21a acquires the amount of reflected light when the focus is correct as well as when the focus is not correct, and creates information where widths of the linear indicator SLP are associated with amounts of light received. With reference to this information, the width of the linear indicator SLP can be determined according to the focus state. If the light receiver includes a two-dimensional sensor (area sensor) instead of the PD sensor 21a, the size of the light spot can be detected directly by the two-dimensional sensor. Accordingly, the linear indicator SLP can be displayed without graphic processing.

Figure 29:
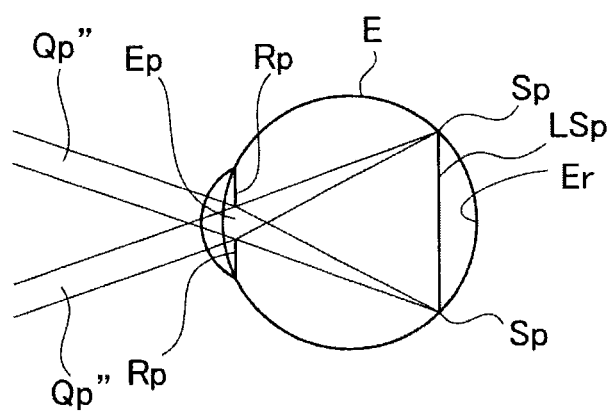
FIG. 29 is a schematic diagram for explaining an example of the operation of the fundus imaging apparatus according to the embodiment.

When the apparatus body is out of focus with respect to the subject's eye E, for example, by manually moving the objective lens 25 back and forth in its optical axis direction, the focus indicator image corresponding to the linear indicator SLP can be made thin, bright, and sharp (see FIG. 29). In this manner, the focus of the apparatus body can be adjusted with respect to the subject's eye E.

Instead of adjusting the focus by manual operation, by detecting the width of the linear indicator SLP, the objective lens 25 may be automatically moved in the optical axis direction so that the line width is reduced (automatic focusing).

(Modification of the Focus Indicator)

Figure 30:
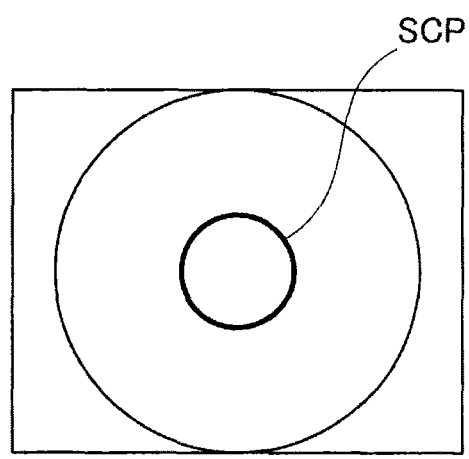
FIG. 30 is a schematic diagram for explaining an example of the operation of the fundus imaging apparatus according to the embodiment.
Figure 31:
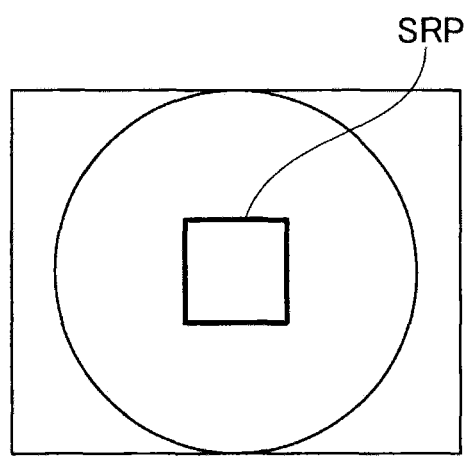
FIG. 31 is a schematic diagram for explaining an example of the operation of the fundus imaging apparatus according to the embodiment.
Figure 32:
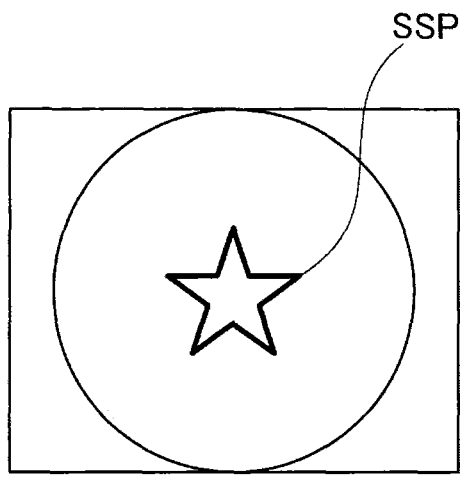
FIG. 32 is a schematic diagram for explaining an example of the operation of the fundus imaging apparatus according to the embodiment.

The focus indicator is not limited to the linear indicator SLP. The focus indicator may also be, for example, a ring-shaped indicator SCP as illustrated in FIG. 30, a square-shaped indicator SRP as illustrated in FIG. 31, a star-shaped indicator SSP as illustrated in FIG. 32, or the like.

As described above, the fundus imaging apparatus of the embodiment is configured to form an alignment indicator and a focus indicator on the fundus Er by using a scanning optical system for scanning the fundus Er. Thus, a wide variety of indicators can be formed.

Although the indicators are described above as being formed by infrared light, this is not so limited. For example, the indicators may be formed by using at least one of red light (R light), green light (G light), and blue light (B light). The amount of light applied at this time is set to a low level not to damage the subject's eye E.

As described above, a focus indicator is formed by projecting a low amount of visible light onto the subject's eye E to perform focusing. Thereby, the subject can perform the focus adjustment on his/her own.

(Presentation of a Fixation Target)

In this embodiment, a fixation target can be projected on the fundus Er during the observation of the fundus Er. This process is performed by the control circuit 27 controlling the lighting control circuit 28.

Figure 33:
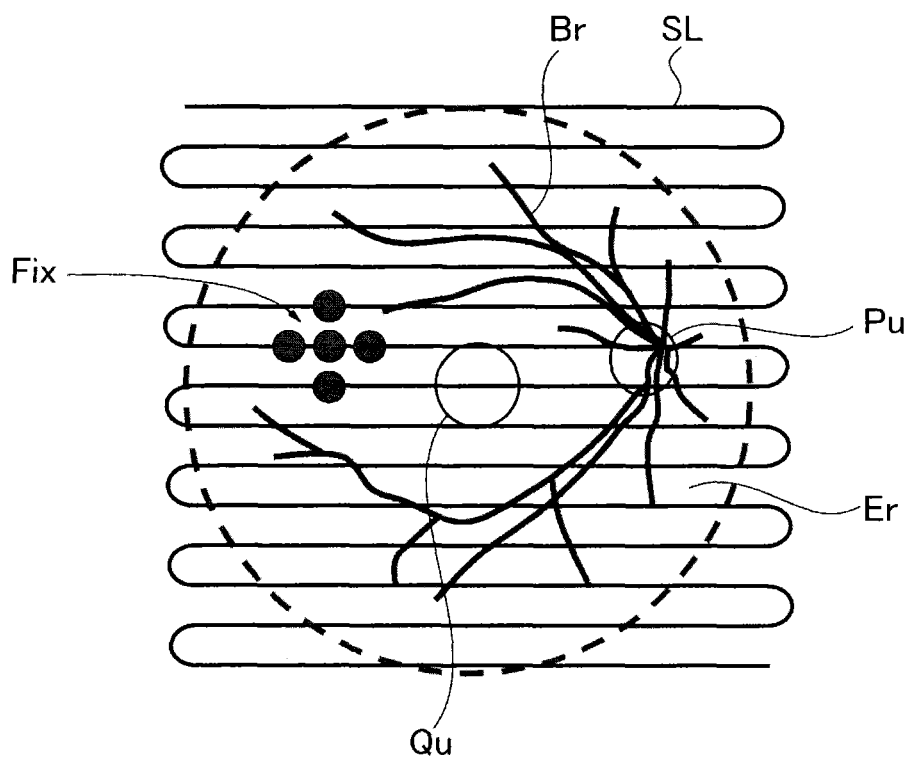
FIG. 33 is a schematic diagram for explaining an example of the operation of the fundus imaging apparatus according to the embodiment.

Described below is a specific example of the process. The control circuit 27 is provided with a fixation target presentation program. While performing a scan along the scan locus SL for fundus observation, the optical scanning ophthalmoscope controls the lighting timing of the red light source 20r or the like such that a cross fixation target Fix as illustrated in FIG. 33 is formed in a scanning locus position corresponding to a site of the fundus Er to be photographed (fixation position). With this, the light spot Sp is formed by a low amount of R light on the fundus Er. Incidentally, the fixation target is formed with visible light so that the subject can recognize it.

Figure 34:
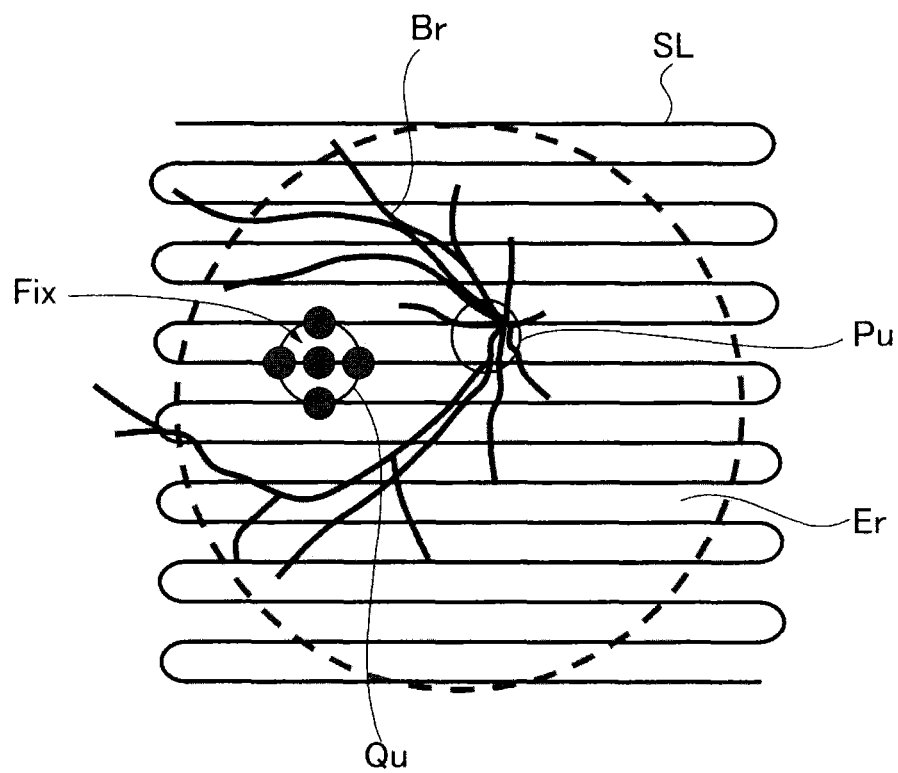
FIG. 34 is a schematic diagram for explaining an example of the operation of the fundus imaging apparatus according to the embodiment.

As illustrated in FIG. 34, the subject turns the eye ball to view the cross fixation target Fix. Then, imaging is performed while visual fixation is being held on the cross fixation target Fix. In this embodiment, the fixation target is drawn on the fundus Er by using a scanning optical system for the scanning of the fundus Er. Therefore, a wide variety of fixation targets can be formed.

(Order of Photographing the Fundus Er)

While the fundus observation and photography have been described first for convenience of explanation, the actual test is performed in the following procedure, for example:

(Step S1)

The power button B is turned on.

(Step S2)

The optical scanning ophthalmoscope is placed in front of the subject's eye E such that the eyepiece tube 3 faces the subject's eye E to be photographed.

(Step S3)

The optical scanning ophthalmoscope body 1 is aligned with respect to the subject's eye E by using the alignment button 10.

(Step S4)

The focus is adjusted for the fundus Er of the subject's eye E by using the focus button 11.

(Step S5)

In response to the completion of the alignment and focusing, the operation mode of the optical scanning ophthalmoscope automatically switches to the observation mode. Along with the transition to the observation mode, a fixation target is projected on the fundus Er. The position to present the fixation target may be changed manually. Further, a fixation target program may be incorporated in advance for enabling a plurality of presentation positions to be selectively applied.

(Step S6)

In response to operation on the photographing button 9, the optical scanning ophthalmoscope performs photographing, and stores the acquired fundus image EGr in the built-in memory 29b.

The embodiment described above can be applied to portable fundus imaging apparatuses.

In this embodiment, in consideration of that the eyepiece tube 3 is located on the left side of the optical scanning ophthalmoscope body 1 when viewed from the examiner's side, the handle 2 is also located on the left side. However, the handle 2 may be provided in the center in the lateral width direction of the optical scanning ophthalmoscope body 1.

Besides, the eyepiece tube 3 as well as the handle 2 may be provided in the center in the lateral width direction of the optical scanning ophthalmoscope body 1.

Further, when the handle 2 is arranged in the center in the lateral width direction of the optical scanning ophthalmoscope body 1, the eyepiece tube 3 may be arranged symmetrically on the left and right sides of the center as a reference.

SECOND EMBODIMENT

While, in the first embodiment, the optical scanning ophthalmoscope is described as an example of the fundus imaging apparatus, the fundus imaging apparatus is not limited to the optical scanning ophthalmoscope. The fundus imaging apparatus may be, for example, an optical coherence tomography apparatus described in the background art. More generally, a fundus imaging apparatus of the embodiment may only be configured to scan a fundus with light, detect return light from the fundus, and image the fundus based on its detection result and the position of a scanning locus.

The optical coherence tomography apparatus of the embodiment may be portable (accordingly, the configuration as illustrated in FIGS. 1 to 6 in the first embodiment can be applied). The optical coherence tomography apparatus may also be for both portable and stationary use, or stationary use only.

The optical coherence tomography apparatus is a device to acquire morphological information such as a cross sectional image and three-dimensional image data of the subject's eye, and/or functional information such as the state of blood flow using an interference optical system. Such optical measurement is called optical coherence tomography (OCT). As the types of OCT systems, time domain OCT and Fourier domain OCT are known. Examples of the Fourier domain OCT include spectral domain OCT using a spectrometer with a low coherence light source (broadband light source) and swept source OCT using a wavelength tunable light source (wavelength variable light source).

Although the following embodiment is described in detail as being applied to the spectral domain OCT, it may also be applicable to fundus imaging apparatuses using other types of OCT.

[Configuration]

Described below is the configuration of the fundus imaging apparatus according to the embodiment. A fundus imaging apparatus 100 illustrated in FIG. 35 includes an optical unit 110, a computer 200, and a user interface (UI) 300. The fundus imaging apparatus 100 replaces the optical scanning ophthalmoscope body 1 of the first embodiment.

The optical unit 110, the computer 200, and the user interface 300 may be integrally provided (i.e., in a single housing). Alternatively, they may be distributed to two or more housings. In this case, part of the fundus imaging apparatus may be provided to another device. For example, part or all of the computer 200 may be provided in a personal computer or a portable terminal (tablet computer, cellular phone, smart phone, etc.). Further, part or all of the user interface 300 may be provided in a personal computer, a portable terminal, a television receiver, a smart TV, and the like.

[Optical Unit 110]

The optical unit 110 includes an optical system for performing OCT measurements and a mechanism for driving a predetermined optical element. The optical system splits light from a light source 111 into measurement light and reference light such that the reference light and return light of the measurement light from the subject's eye E interfere with each other, and detects the interference light. The optical system has the same configuration as the conventional spectral domain OCT. That is, the optical system is configured to divide low coherence light (broadband light) into reference light and measurement light such that the measurement light having traveled via the subject's eye E and the reference light having passed through a reference optical path interfere with each other to generate interference light, and detect spectral components of the interference light. The result of detecting spectral components (detection signal) is sent to the computer 200.

When the swept source OCT is used, a wavelength tunable light source is provided instead of a low coherence light source, and an optical member for the spectral resolution of interference light is not provided. In general, regarding the configuration of the optical unit 110, any known techniques may be applicable depending on the type of the OCT.

The light source 111 outputs broadband low coherence light. The low coherence light includes, for example, wavelengths of a near-infrared region (about 800 nm to 900 nm), and has a temporal coherence length of approximately several tens of micrometers. The near-infrared light having wavelengths not visible to human eyes, for example, with a center wavelength of approximately 1040 nm to 1060 nm, can be used as the low coherence light.

The light source 111 includes an optical output device such as super luminescent diode (SLD), LED, semiconductor optical amplifier (SOA), or the like.

The low coherence light output from the light source 111 is collimated into a parallel light flux by a collimator lens 112, and is guided to a beam splitter 113. The beam splitter 113 is, for example, a half mirror that reflects a predetermined fraction of light and transmits the rest. The beam splitter 113 splits the parallel light flux into measurement light and reference light.

The measurement light is irradiated to the subject's eye E (also referred to as signal light). A group of optical elements that constitutes the optical path of the measurement light (measurement optical path) is referred to as measurement arm (also referred to sample arm). The reference light serves as a reference to extract information contained in return light of the measurement light as an interference signal. A group of optical elements that constitutes the optical path of the reference light (reference optical path) is referred to as the reference arm.

One end of the reference optical path is the beam splitter 113 and the other end is a reference mirror 114. The reference light consisting of components having transmitted through the beam splitter 113 is reflected by the reference mirror 114 and returns to the beam splitter 113.

Figure 36:
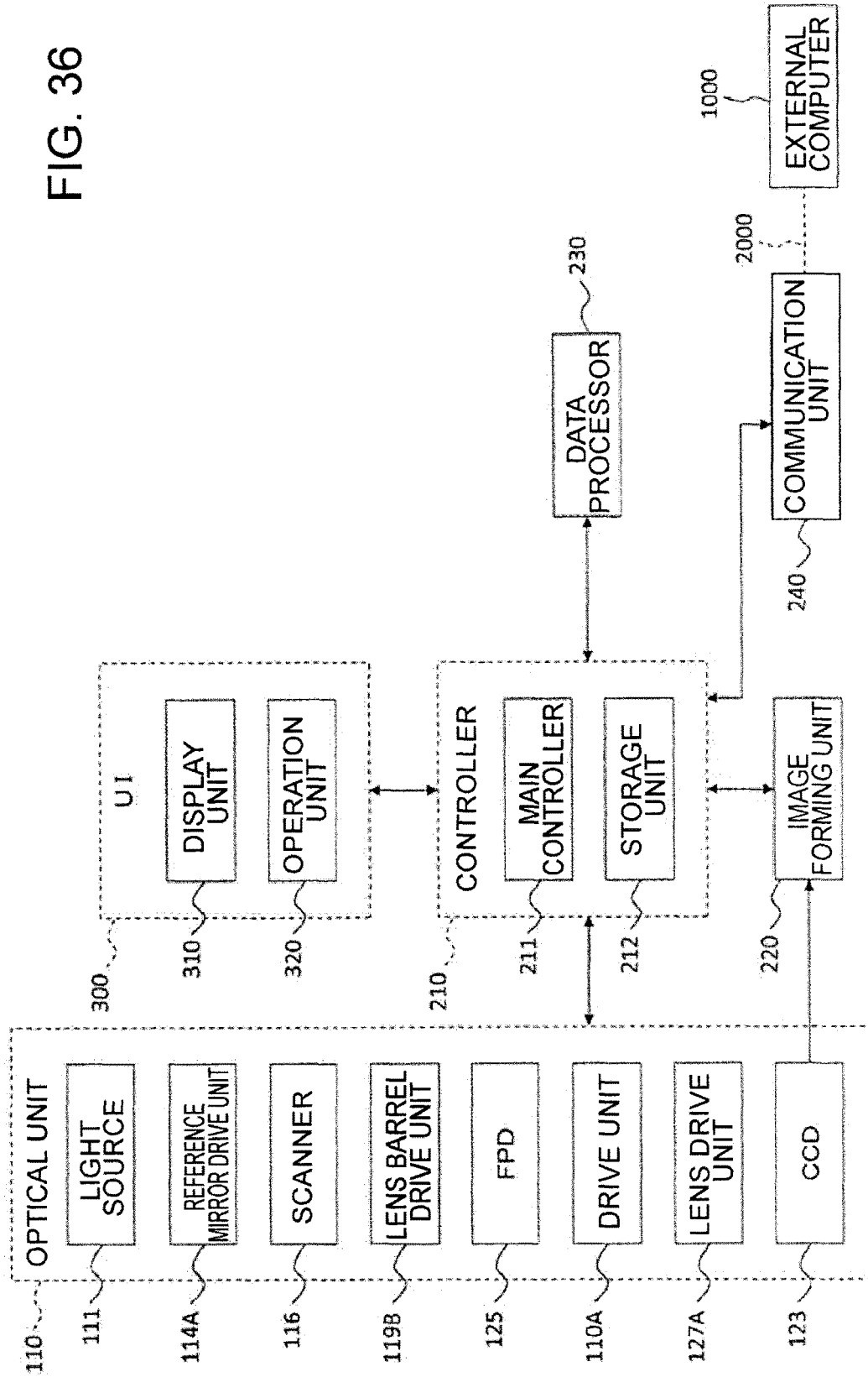
FIG. 36 is a schematic diagram illustrating an example of the configuration of a fundus imaging apparatus according to an embodiment.

The reference mirror 114 is moved along the traveling direction of the reference light by a reference mirror drive unit 114A illustrated in FIG. 36. Thereby, the length of the reference optical path is changed. The reference mirror drive unit 114A functions such that the length of the measurement optical path and that of the reference optical path relatively change. This changes the depth where the interference intensity of the measurement light and the reference light is the maximum.

While this embodiment employs a configuration in which the length of the reference optical path is changed, instead of or in addition to this configuration, a configuration may be applied in which the length of the measurement optical path is changed. The length of the measurement optical path can be changed by employing, for example: a corner cube that reflects incident measurement light in the opposite direction to the incident direction thereof; and a mechanism for moving the corner cube in the incident direction and the reflection direction.

The measurement light consisting of components reflected on the beam splitter 113 is deflected by a fixed mirror 115 that is arranged as being tilted with respect to the measurement optical path, and is guided to a scanner 116. The scanner 116 is, for example, a two-axis optical scanner. In other words, the scanner 116 is configured to be capable of two-dimensionally deflecting the measurement light. The scanner 116 is, for example, a mirror scanner including two mirrors capable of deflection in directions perpendicular to each other. This mirror scanner may be, for example, micro electro mechanical systems (MEMS). As another example, the scanner 116 may be configured with a single mirror scanner and a rotary prism.

The measurement light output from the scanner 116 is two-dimensionally deflected collimated light. The measurement light is focused by a relay lens 117, and forms an image in the air in a plane Pc conjugate to the fundus Ef (fundus conjugate plane). In addition, the measurement light is focused again by an objective lens 119 having a function as a focusing lens, and is incident on the subject's eye E. Incidentally, an optical element (dichroic mirror 118) located on the fundus conjugate plane Pc is described later. When a switchable lens 127 (described later) is arranged in the measurement optical path, the measurement light that has passed through the objective lens 119 enters the subject's eye E as being refracted by the switchable lens 127.

The objective lens 119 and a lens barrel 119A are moved along the measurement optical path by a lens barrel drive unit 119B illustrated in FIG. 36. The objective lens 119 and the lens barrel 119A are moved in the optical axis direction according to the refractive power of the subject's eye E. Thereby, the fundus conjugate plane Pc is arranged in a position conjugate to the fundus Ef. As a result, the measurement light is projected onto the fundus Ef as a light spot. Incidentally, a focusing lens may be provided aside from the objective lens 119.

The switchable lens 127 is used for changing the site (depth position) of the subject's eye E to be imaged. Examples of the site to be imaged include the fundus Ef, the anterior segment, the crystalline lens, the vitreous body, and the like. When the fundus Ef is switched to the anterior segment or vice versa, as in the first embodiment, the projection lens LL for anterior segment imaging is used as the switchable lens 127. The switchable lens 127 is inserted/retracted with respect to the measurement optical path by a lens drive unit 127A illustrated in FIG. 36. If there are three or more sites of interest, it is possible to arrange two or more switchable lenses that can be selectively placed on the optical path. Besides, for example, it is also possible to use as the switchable lens 127 an optical element having a variable refractive power like Alvarez Lens, for example. In this embodiment, the switchable lens 127 is retracted from the optical path when imaging the fundus Ef, and the switchable lens 127 is placed in the optical path when imaging the anterior segment.

Measurement light irradiated to the fundus Ef is scattered (reflected) at various depth positions of the fundus Ef. Backscattered light (return light) of the measurement light from the fundus Ef travels back in the reverse direction through the same path as in forward travel and is guided to the beam splitter 113.

Figure 35:
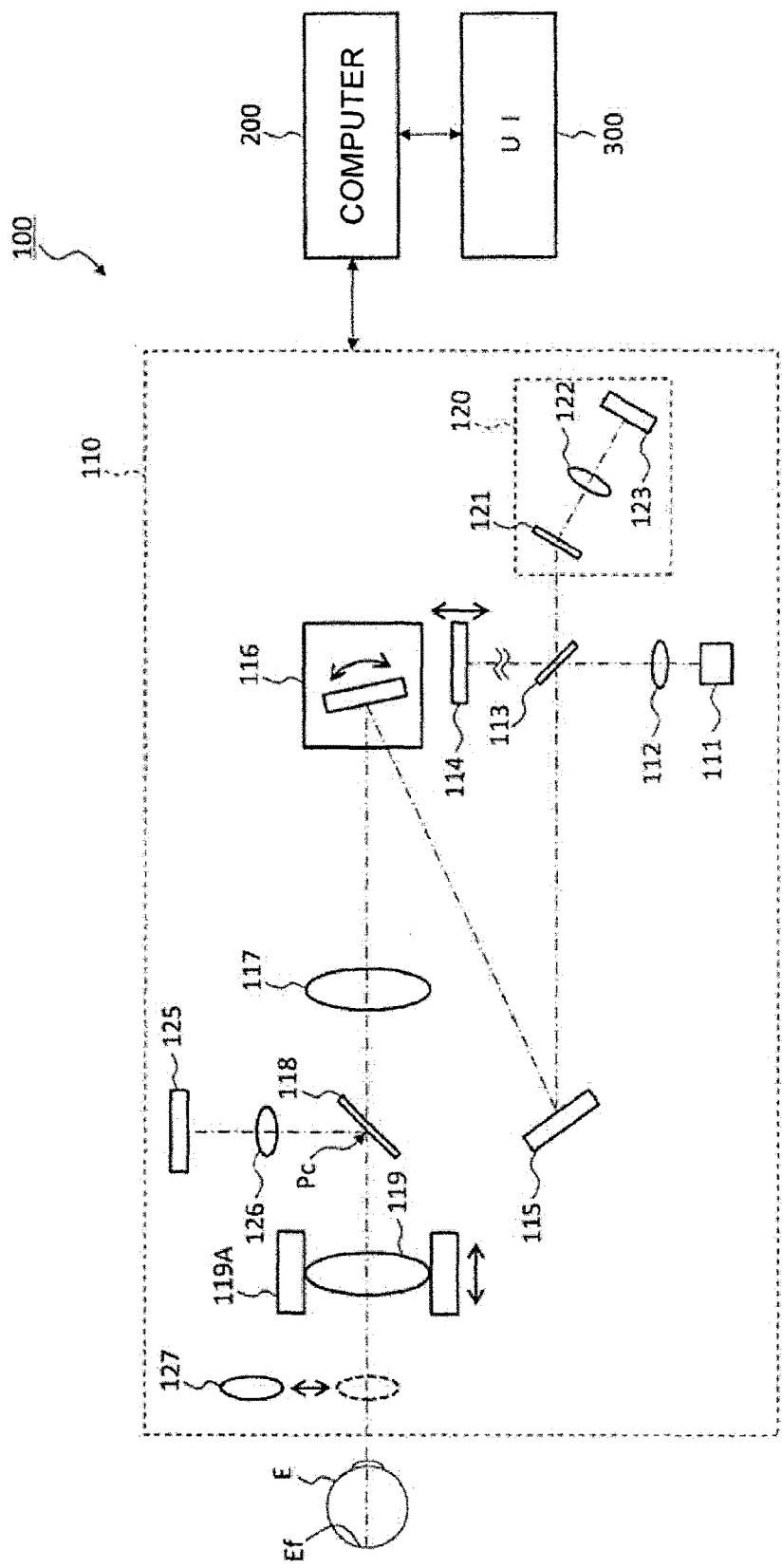
FIG. 35 is a schematic diagram illustrating an example of the configuration of a fundus imaging apparatus according to an embodiment.

The beam splitter 113 causes the return light of the measurement light and the reference light having passed through the reference optical path to interfere with each other. At this time, only return light components having passed through a distance approximately equal to the length of the reference optical path, that is, only backscattered light from a range within the coherence length with respect to the length of the reference optical path, substantially interferes with the reference light. Interference light generated via the beam splitter 113 is guided to a spectroscope 120. The interference light incident on the spectroscope 120 is resolved into spectra by a diffraction grating 121, and is irradiated to the light receiving surface of a CCD image sensor 123 through a lens 122. While the diffraction grating 121 illustrated in FIG. 35 is a transmission grating, the diffraction grating 121 may be other spectral element such as a reflective diffraction grating or the like.

The CCD image sensor 123 is, for example, a line sensor or an area sensor, and detects the spectral components of the interference light to convert them to electric charges. The CCD image sensor 123 accumulates the electric charges to generate a detection signal and sends it to the computer 200.

As mentioned above, in the position corresponding to the fundus conjugate plane Pc on the measurement optical path, the dichroic mirror 118 is arranged obliquely. The dichroic mirror 118 is configured to transmit therethrough the measurement light in the near-infrared band and reflect light in the visible band.

A flat panel display (FPD) 125 and a lens 126 are arranged on the optical path branched from the measurement optical path via the dichroic mirror 118. The flat panel display 125 displays information under the control of a controller 210. The information displayed on the flat panel display 125 includes various indicators to be presented to the subject's eye E. Examples of such indicators include a fixation target for visual fixation of the subject's eye E. The flat panel display 125 may also display information such as instructions on a test and the like.

The flat panel display 125 is located in a position conjugate to the fundus conjugate plane Pc (accordingly, a position conjugate to the fundus Ef) through the lens 126. The flat panel display 125 may be, for example, a liquid crystal display (LCD) or an organic EL display (OELD).

Visible light output from the flat panel display 125 is reflected by the dichroic mirror 118 through the lens 126. The visible light is then incident into the subject's eye E through the objective lens 119 and reaches the fundus Ef. Thereby, an image (e.g., a fixation target) is projected onto the fundus Ef based on the visible light.

Instead of the dichroic mirror 118, an optical element such as a half mirror may be provided. It is also possible to provide a reflecting mirror configured to be inserted/retracted with respect to the measurement optical path. If the dichroic mirror 118 or a half mirror is provided, OCT measurement can be performed simultaneously with the projection of an indicator. On the other hand, if a reflecting mirror is provided, OCT measurement and the projection of an indicator are performed at different timings.

While, in this embodiment, a Michelson interferometer is employed, any type of interferometer such as, for example, a Mach-Zehnder interferometer may be used as appropriate. Besides, instead of the CCD image sensor, other light receiving elements, such as a complementary metal oxide semiconductor (CMOS) image sensor may be used.

In this embodiment, light reflected by the beam splitter 113 is used as the measurement light, and light having transmitted through the beam splitter 113 is used as the reference light. In an opposite manner, the light reflected by the beam splitter 113 may be used as the reference light, and the light having transmitted through the beam splitter 113 may be used as the measurement light. In this case, the arrangement of the measurement arm and the reference arm is reversed to that of FIG. 35.

A member may be provided to change the characteristics of the measurement light and/or the reference light. For example, an optical attenuator and a polarization adjuster (polarization controller) may be provided to the reference optical path. The optical attenuator adjusts the amount of the reference light under the control of the computer 200. The optical attenuator includes, for example, a neutral density filter and a mechanism for inserting/retracting the filter with respect to the reference optical path. The polarization adjuster adjusts the polarization state of the reference light under the control of the computer 200. The polarization adjuster includes, for example, a polarizing plate arranged in the reference optical path, and a mechanism for rotating it. These are used to adjust the interference intensity of the return light of the measurement light and the reference light.

A front image acquisition optical system may be provided for acquiring a front image by photographing the subject's eye E. The front image is an image of the anterior segment or the fundus Ef. The front image acquisition optical system forms an optical path branched from the measurement optical path, and, for example, includes the same illumination optical system and photographing optical system as those of a conventional retinal camera. The illumination optical system irradiates illumination light consisting of (near) infrared light or visible light to the subject's eye E. The photographing optical system detects return light (reflected light) of the illumination light from the subject's eye E. The photographing optical system includes a focusing lens in common with the measurement optical path, and/or a focusing lens independent of the measurement optical path. The photographing optical system includes a focusing lens in common with the measurement optical path (the objective lens 119, the switchable lens 127, etc.), and/or a focusing lens independent of the measurement optical path. As another example of the front image acquisition optical system, the same optical system as in a conventional SLO may be employed.

If the front image acquisition optical system is provided, the same alignment optical system as in a conventional retinal camera may be provided. The alignment optical system forms an optical path branched from the measurement optical path, and generates an indicator (alignment indicator) for the alignment of the apparatus optical system with respect to the subject's eye E. The alignment is a position matching in a direction (referred to as xy direction) along a plane perpendicular to the measurement optical path (the optical axis of the objective lens 119). Although not illustrated, the alignment optical system generates two alignment light fluxes by a two-hole aperture from a light flux output from the alignment light source (LED, etc.). The two alignment light fluxes are guided to the measurement optical path via the beam splitter that is arranged inclined with respect to the measurement optical path, and are projected onto the cornea of the subject's eye E. Corneal reflection light beams of the alignment light fluxes are detected by the image sensor of the front image acquisition optical system.

If the alignment optical system is provided, it is possible to perform automatic alignment. Specifically, a data processor 230 of the computer 200 analyzes a signal fed from the image sensor of the front image acquisition optical system, and specifies the locations of two alignment indicator images. Further, based on the locations of the two alignment indicator images specified, the controller 210 moves the optical unit 110 in the xy direction such that two corneal reflection light beams are projected onto a predetermined position (e.g., the center) on the light receiving surface of the image sensor as being overlapped one on the other. The optical unit 110 is moved by a drive unit 110A.

In addition, if the front image acquisition optical system is provided, the same focusing optical system as in a conventional retinal camera may be provided. The focusing optical system forms an optical path branched from the measurement optical path, and generates indicators (focus indicator, split target) for performing focusing on the fundus Ef. Although not illustrated, the focusing optical system generates two focusing light fluxes from light fluxes output from the focusing light source (LED, etc.) by the split target plate. The two focusing light fluxes are guided to the measurement optical path via a reflecting member that is arranged inclined to the measurement optical path, and is projected onto the fundus Ef. Fundus reflection light beams of the focusing light fluxes are detected by the image sensor of the front image acquisition optical system.

If the focusing optical system is provided, it is possible to perform automatic focusing. Specifically, the data processor 230 of the computer 200 analyzes a signal fed from the image sensor of the front image acquisition optical system, and specifies the locations of two split target images. Further, based on the locations of the two split target images specified, the controller 210 performs control of the movement of the focusing optical system and control of the focusing lens (e.g., control of the movement of the objective lens 119) such that two fundus reflection light beams are projected in a straight line on the light receiving surface of the image sensor.

If the front image acquisition optical system is provided, it is possible to perform automatic tracking. The automatic tracking is intended to move the optical unit 110 in accordance with the movement of the subject's eye E. For performing the automatic tracking, alignment and focusing are performed in advance. For example, the automatic tracking is performed as follows. First, a moving image of the subject's eye E is captured by the front image acquisition optical system. The data processor 230 sequentially analyzes frames of the moving image to monitor the movement (change in position) of the subject's eye E. The controller 210 controls the drive unit 110A to move the optical unit 110 according to the positions of the subject's eye E sequentially acquired. With this, the optical unit 110 follows the movement of the subject's eye E in real time. Thus, it is possible to maintain a suitable positional relationship aligned with the subject in focus.

Note that, in this embodiment, an indicator can be projected on the fundus Ef using measurement light deflected by the scanner 116 without dedicated optical systems for projecting an alignment indicator, a focus indicator and a fixation target. This process is described later.

[Control System, Data Processing System]

Described below are the control system and the data processing system of the fundus imaging apparatus 100 of the embodiment. FIG. 36 illustrates an example of the configuration of the control system and the data processing system.

The center of the control system and the data processing system is the computer 200. The computer 200 includes a microprocessor, RAM, ROM, a hard disk drive, a communication interface, and so on. A storage device such as a hard disk drive stores a computer program for causing the fundus imaging apparatus 100 to implement various processes. The computer 200 may include a dedicated circuit board to perform a specific process. For example, the computer 200 may be provided with a circuit board to perform a process of forming an OCT image.

(User Interface 300)

The user interface 300 is connected to the computer 200. The user interface 300 includes a display unit 310 and an operation unit 320. The display unit 310 includes a display device such as a flat panel display or the like. The operation unit 320 includes operation devices such as buttons, keys, a joystick, an operation panel, and the like arranged on the housing or the outside of the fundus imaging apparatus 100. If the computer 200 includes a personal computer, the operation unit 320 may include the operation devices of the personal computer (a mouse, a keyboard, a track pad, buttons, etc.).

The display unit 310 and the operation unit 320 need not be configured as individual devices. They may be a device having integrated functions of display and operation such as a touch panel. In this case, the operation unit 320 includes a touch panel and a computer program. The content of operation on the operation unit 320 is input to the controller 210 as an electrical signal. Operation and information input may be performed by using a graphical user interface (GUI) displayed on the display unit 310 and the operation unit 320.

(Controller 210)

The controller 210 is provided to the computer 200. The controller 210 includes a microprocessor, RAM, ROM, a hard disk drive, and so on. The controller 210 is provided with a main controller 211 and a storage unit 212.

(Main Controller 211)

The main controller 211 controls each unit of the fundus imaging apparatus 100. For example, the main controller 211 controls those including the drive unit 110A, the light source 111, the reference mirror drive unit 114A, the scanner 116, the lens barrel drive unit 119B, the CCD (image sensor) 123, the flat panel display 125, the display unit 310, the data processor 230, and a communication unit 240.

The drive unit 110A includes a mechanism for moving the optical unit 110 in a direction (z direction) along the measurement optical path (the optical axis of the objective lens 119), and in a direction along a plane perpendicular to the z direction (xy direction). The reference mirror drive unit 114A is configured to move the reference mirror 114 along the reference optical path. The lens barrel drive unit 119B is configured to move the objective lens 119 and the lens barrel 119A along the measurement optical path. The lens drive unit 127A is configured to insert/remove the switchable lens 127 into/from the measurement optical path.

(Storage Unit 212)

The storage unit 212 stores various types of data. The storage unit 212 also stores various programs and data for operating the fundus imaging apparatus 100. The data stored in the storage unit 212 includes data acquired by the fundus imaging apparatus 100 and data stored in advance.

Examples of the data acquired by the fundus imaging apparatus 100 include image data of an OCT image, test data, image data of a front image, and the like. The test data is data indicating the state of the subject's eye that is generated by processing the detection result of interference light by the optical unit 110. The storage unit 212 stores in advance setting information as described below.

(Setting Information)

The setting information indicates the contents of settings of predetermined items related to the optical unit 110 and the data processor 230. The setting information includes setting contents related to at least one of the following items: (1) fixation position; (2) scan pattern; (3) focus position; (4) diopter correction; (5) maximum interference depth; and (6) analysis process.

(1) The "fixation position" indicates a direction in which the vision of the subject's eye E is fixed, i.e., the site of the subject's eye E where OCT measurement is performed. Examples of the fixation position include a fixation position for performing OCT measurement of the macula and around it, a fixation position for performing OCT measurement of the optic disc and around it, a fixation position for performing OCT measurement of the macula, the optic disc, and around them, and the like. It is also possible to set a fixation position corresponding to an arbitrary portion of the subject's eye E. The fixation position includes, for example, information indicating the display position of a fixation target (the position of pixels) on the flat panel display 125.

(2) The "scan pattern" indicates a pattern along which the projection position of measurement light for the subject's eye E is to be moved. Examples of the scan pattern include one or more line scans (horizontal scan, vertical scan), one or more cross scans, radial scan, circle scan, and the like. Further, to obtain a three-dimensional image (three-dimensional data set), three-dimensional scan is applied in which intervals of a plurality of line scans are set to be sufficiently narrow.

(3) The "focus position" indicates the focus conditions applied to OCT measurement. The focus position includes, for example, information indicating the position of the objective lens 119.

(4) The "diopter correction" indicates conditions applied to diopter correction. Specifically, examples of the diopter correction includes a value indicating the refractive power (visual acuity) of the subject's eye E, information indicating the position of the objective lens 119, and the like.

(5) The "maximum interference depth" indicates a depth applied to OCT measurement in which the intensity of interference between measurement light and reference light is the maximum. The maximum interference depth includes, for example, information indicating the position of the reference mirror 114.

(6) The "analysis process" indicates contents of processing to be performed based on data obtained by the optical unit 110, i.e., the types of test data acquired. Examples of the analysis process include fundus layer thickness analysis, (optic) disc shape analysis, and the like. The fundus layer thickness analysis refers to an analysis for finding the thickness of a predetermined layer tissue of the fundus (retina, retinal subtissue, choroid, sclera, etc.). The optic disc shape analysis refers to an analysis for finding the shape of the optic disc by analyzing a cross sectional image, a three-dimensional image etc. of the fundus, and detecting the hole (cut, missing site) of the retina. In the optic disc shape analysis, the slope of the optic disc (asymmetry of the shape) may also be obtained.

The analysis process may include the process of specifying an image region corresponding to a predetermined site of the subject's eye E, the process of obtaining the shape or distribution of the specified image region. Examples of the predetermined site to be specified include, for example, blood vessel, optic disc, macula, predetermined layer tissue (retina, retinal subtissue, choroid, sclera, etc.), a laser treatment scar, a lesion (drusen, retinal detachment site, tissue defect site, tissue deformation site, etc.).

The analysis process may include the process of calculating a distance based on data obtained by OCT measurement. Examples of such distance measurement include measurement of intraocular distance (eye axial length. etc.) based on data acquired by the OCT measurement of the anterior segment and data acquired by the OCT measurement of the fundus. In addition, the intraocular distance may be found based only on an OCT image of the fundus or the anterior segment.

When OCT measurement is performed for both the left eye and the right eye of the subject, especially, if different settings are applied to the left and right eyes, setting information for the left eye (left-eye setting information), and setting information for the right eye (right-eye setting information) may be provided separately.

When the fundus imaging apparatus 100 is shared by two or more subjects, especially, if different settings are applied to the subjects, individual setting information may be provided for each of the subjects. The setting information is created based on, for example, examination results and/or diagnosis results for the subject's eye obtained in the past.

(Image Forming Unit 220)

An image forming unit 220 forms image data based on a detection signal from the CCD image sensor 123. This process includes, as in conventional spectral domain OCT, noise removal (noise reduction), filtering, dispersion compensation, fast Fourier transform (FFT), and so on. If OCT of another type is applied, the image forming unit 220 performs known processing according to the type.

The image forming unit 220 includes, for example, a dedicated circuit board and/or a microprocessor. Here, "image data" may be equated with "image" based on the image data.

(Data Processor 230)

The data processor 230 performs various types of data processing. For example, the data processor 230 performs image processing on an image formed by the image forming unit 220. As an example, the data processor 230 may form image data of a three-dimensional image of the subject's eye E based on a plurality of two-dimensional cross sectional images at different cross sectional positions. The image data of a three-dimensional image refers to image data in which the position of pixels is defined by a three-dimensional coordinate system. Examples of the image data of a three-dimensional image include image data formed of three-dimensional arrays of voxels. The image data is referred to as volume data or voxel data. To display an image based on volume data, the data processor 230 performs rendering on the volume data (volume rendering, maximum intensity projection (MIP), etc.), and forms image data of a pseudo three-dimensional image viewed from a particular direction.

The data processor 230 is capable of imaging an arbitrary cross section of the three-dimensional image (multi-planar reconstruction: MPR).

Besides, stack data of a plurality of cross sectional images may be formed as the image data of a three-dimensional image. The stack data is image data obtained by three-dimensionally arranging a plurality of cross sectional images obtained along a plurality of scan lines based on the positional relationship of the scanning lines. That is, the stack data is image data obtained by representing a plurality of cross sectional images, which are originally defined by individual two-dimensional coordinate systems, by a single three-dimensional coordinate system (i.e., embedding the cross sectional images in one three-dimensional space). The data processor 230 is capable of performing MPR processing based on the stack data.

The data processor 230 includes, for example, a microprocessor, RAM, ROM, a hard disk drive, a dedicated circuit board for predetermined data processing, and the like. A storage device such as a hard disk drive stores in advance computer programs for causing the microprocessor to perform data processing described below.

(Communication Unit 240)

The communication unit 240 performs data communication with an external device. The data communication may be performed by an arbitrary method. For example, the communication unit 240 includes a communication interface compatible with the Internet, a communication interface that compatible with LAN, a communication interface compatible with short-range communication, and the like. Besides, the data communication may be wireless communication or wired communication.

The communication unit 240 performs data communication with an external computer 1000 via a communication line 2000. There may be any number, one or more, of the external computers 1000. Examples of the external computer 1000 include a server installed in a medical institution, a terminal used by a doctor, a server of the manufacturer (or, dealer, maintenance service provider, rental service provider, etc.) of the fundus imaging apparatus 100, a terminal used by a person in charge in the manufacturer, and the like. The external computer 1000 is not limited to those that can communicate directly with the fundus imaging apparatus 100, and may be one capable of indirect communication via another computer. In the example described in the first embodiment, the external computer 1000 includes not only the portable information device 16, but also a portable information device 16' and a personal computer 16A.

Data transmitted/received by the communication unit 240 may be encrypted. In this case, the controller 210 (or the data processor 230) includes an encryption processor that encrypts transmission data and a decoder that decodes received data.

[Operations and Effects]

A description is given of the operations and effects of the fundus imaging system of the embodiment. Incidentally, mode of scanning the fundus and mode of forming an indicator on the fundus may be the same as in the first embodiment.

The fundus imaging apparatus (100) of the embodiment includes the following components: a scanning optical system configured to scan a fundus (Ef) of a subject's eye (E) with light from a light source (the light source 111), and receive return light from the fundus by a light receiver (the CCD123); a control circuit (the controller 210) configured to control the scanning optical system such that a scanning locus (scan pattern) is formed by the light on the fundus; and an image forming unit (the image forming unit 220, the data processor 230) configured to form an image of the fundus based a light receiving signal from the light receiver and the position of the scanning locus.

The alignment mode may be provided as the operation mode of the control circuit. In the alignment mode, the control circuit (the controller 210) controls the scanning optical system (especially, controls the scanner 116) to project an alignment indicator for aligning the scanning optical system with the subject's eye on the fundus based on the light (measurement light) from the light source. With this configuration, alignment can be achieved without a dedicated optical system for projecting the alignment indicator.

In the alignment mode, any control mode described in the first embodiment may be employed. Specifically, the following control may be applicable.

In the alignment mode, the image forming unit (the image forming unit 220, etc.) may form an image of the alignment indicator. Further, when the front image acquisition optical system described above is provided, if it is capable of detecting the wavelength bands of measurement light, an image of the alignment indicator may be obtained. The control circuit (the controller 210) displays the image of the alignment indicator formed by the image forming unit on a display (the display unit 310). With this configuration, the user can recognize the state of alignment. The display need not necessarily be configured as part of the fundus imaging apparatus, and may be an external display.

The fundus imaging apparatus of the embodiment may include a drive unit (the drive unit 110A) for moving the scanning optical system. In this case, the control circuit (the controller 210) may include a determination unit configured to determine the state of alignment based on the alignment indicator. The determination unit performs the same processing as with the alignment indicator determination unit 27a of the first embodiment. The control circuit controls the drive unit based on the result of the determination to move the scanning optical system. With this configuration, it is possible to perform automatic alignment based on the alignment indicator.

In the fundus imaging apparatus of the embodiment, the scanning optical system may include a scanner (the scanner 116). In this case, in the alignment mode, the control circuit (the controller 210) controls the scanner to form a different scanning locus from a scanning locus for forming a fundus image in the fundus. Thereby, the alignment indicator can be projected on the fundus. Multiple ring or spiral locus may be cited as the scanning locus to be applied in the alignment mode in addition to the circular locus CRSp illustrated in FIG. 16 etc.

If the scanning optical system includes a scanner (the scanner 116), the control circuit (the controller 210) performs the control of the scanner based on the same scanning locus as the scanning locus for forming a fundus image in cooperation with the control of the lighting timing of the light source (the light source 111), i.e., the synchronous control of the scanner 116 and the light source 111. Thus, the alignment indicator can be projected on the fundus. This process is performed in such a manner illustrated in FIG. 20 etc.

If the scanning optical system include a scanner (the scanner 116), while keeping the light source (the light source 111) on, the control circuit (the controller 210) performs the control of the scanner based on the same scanning locus as the scanning locus for forming a fundus image in cooperation with the control of the output timing of a light receiving signal from the light receiver (the CCD123), i.e., the synchronous control of the scanner 116 and the CCD123. Thus, an image of the alignment indicator can be displayed on the display (the display unit 310). This process is performed in the same manner as in the first embodiment.

In the alignment mode, the light irradiated to the fundus (measurement light) may be infrared light.

The focus mode may be provided as the operation mode of the control circuit (the controller 210). In the focus mode, the scanning optical system is controlled such that the focus indicator for the focusing of the scanning optical system to the fundus of the subject's eye is projected onto the fundus Ef based on light from the light source (the light source 111). With this configuration, focusing can be achieved without a dedicated optical system for projecting a focus indicator.

In the focus mode, the control circuit (the controller 210) may display an image of the focus indicator formed by the image forming unit (the image forming unit 220, the data processor 230) on a display (the display unit 310). With this configuration, the user can recognize the state of focus.

The scanning optical system may include a lens (the objective lens 119, etc.) for focusing. The fundus imaging apparatus may further include a drive unit (the lens barrel drive unit 119B, etc.) for moving the lens in the direction of the optical axis of the scanning optical system. In this case, the control circuit (the controller 210) includes a determination unit configured to determine the state of focus based on the focus indicator. The determination unit performs the same processing as in the first embodiment. The control circuit controls the drive unit based on the result of the determination to move the lens. With this configuration, it is possible to perform automatic focusing based on the focus indicator.

In the focus mode, the light irradiated to the fundus (measurement light) may be infrared light.

The fundus observation mode for observing the moving image of the fundus of the subject's eye may be provided as the operation mode of the control circuit (the controller 210). In the fundus observation mode, scanning is repeated based on the same scan pattern (e.g., line scan, three-dimensional scan). Thereby, a moving image representing substantially the same site of the fundus Ef is displayed. In the fundus observation mode, the control circuit (the controller 210) controls the light source (the light source 111) such that a fixation target of visible light is presented to the subject's eye. If this configuration is applied, the light source 111 is provided with a visible light source capable of outputting visible light, in addition to a near-infrared light source for OCT measurement. The control circuit performs synchronous control between the light source 111 and the scanner 116 to output visible light (and infrared light) when light is irradiated to the scanning locus position corresponding to the fixation target.

THIRD EMBODIMENT

In the third embodiment, a description is given of a fundus imaging system that includes an optical scanning ophthalmoscope similar to that of the first embodiment referring to FIGS. 1 to 9 of the first embodiment as appropriate. The configuration of the optical system is different in part from that of the first embodiment (FIG. 7).

Figure 37:
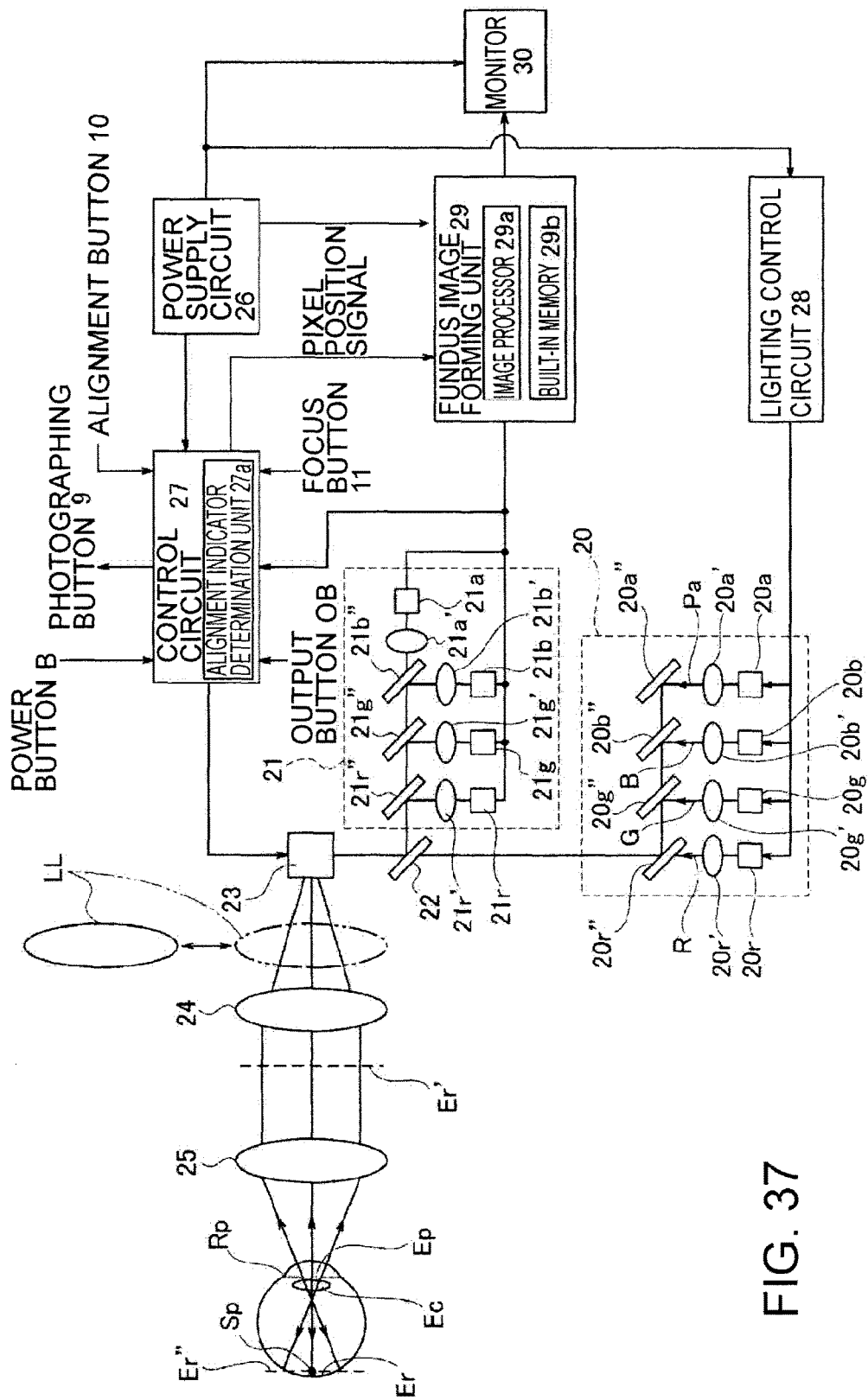
FIG. 37 is a schematic diagram illustrating an example of the configuration of a fundus imaging system according to an embodiment.

FIG. 37 illustrates the configuration of the fundus imaging apparatus according to this embodiment. The configuration illustrated in FIG. 37 is different from that of FIG. 7 of the first embodiment in the presence of a projection lens LL. The projection lens LL is described later.

With the optical scanning ophthalmoscope of this embodiment, the subject can perform fundus photography on his/her own. In such a case, a fundus image may be associated with personal information in the following manner.

(Example of Process of Acquiring Personal Information)

Figure 38:
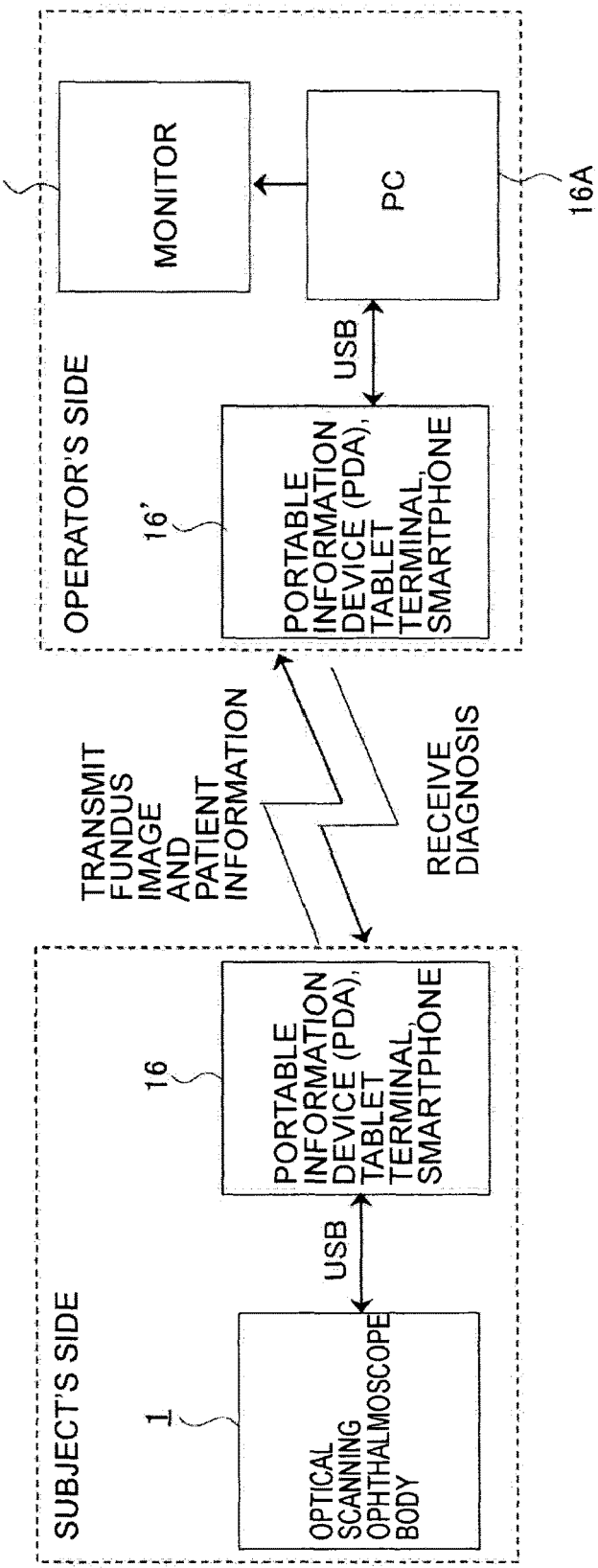
FIG. 38 is a schematic diagram illustrating an example of the configuration of a fundus imaging system according to an embodiment.

As schematically illustrated in FIG. 38, the optical scanning ophthalmoscope body 1 is connected to the portable information device 16 via USB. In the medical institution (the examiner's side), the portable information device 16', the personal computer 16A (PC), and a monitor 16B is installed. The portable information device 16' is connected to the personal computer 16A via USB. The portable information device 16' on the examiner's side receives information sent from the portable information device 16 on the subject's side.

The personal computer 16A includes an analyzer that analyzes information of a fundus image and personal information. The monitor 16B is connected to the personal computer 16A. The fundus image and the personal information are displayed in association on the screen of the monitor 16B if necessary.

CONFIGURATION EXAMPLE 1

Figure 39:
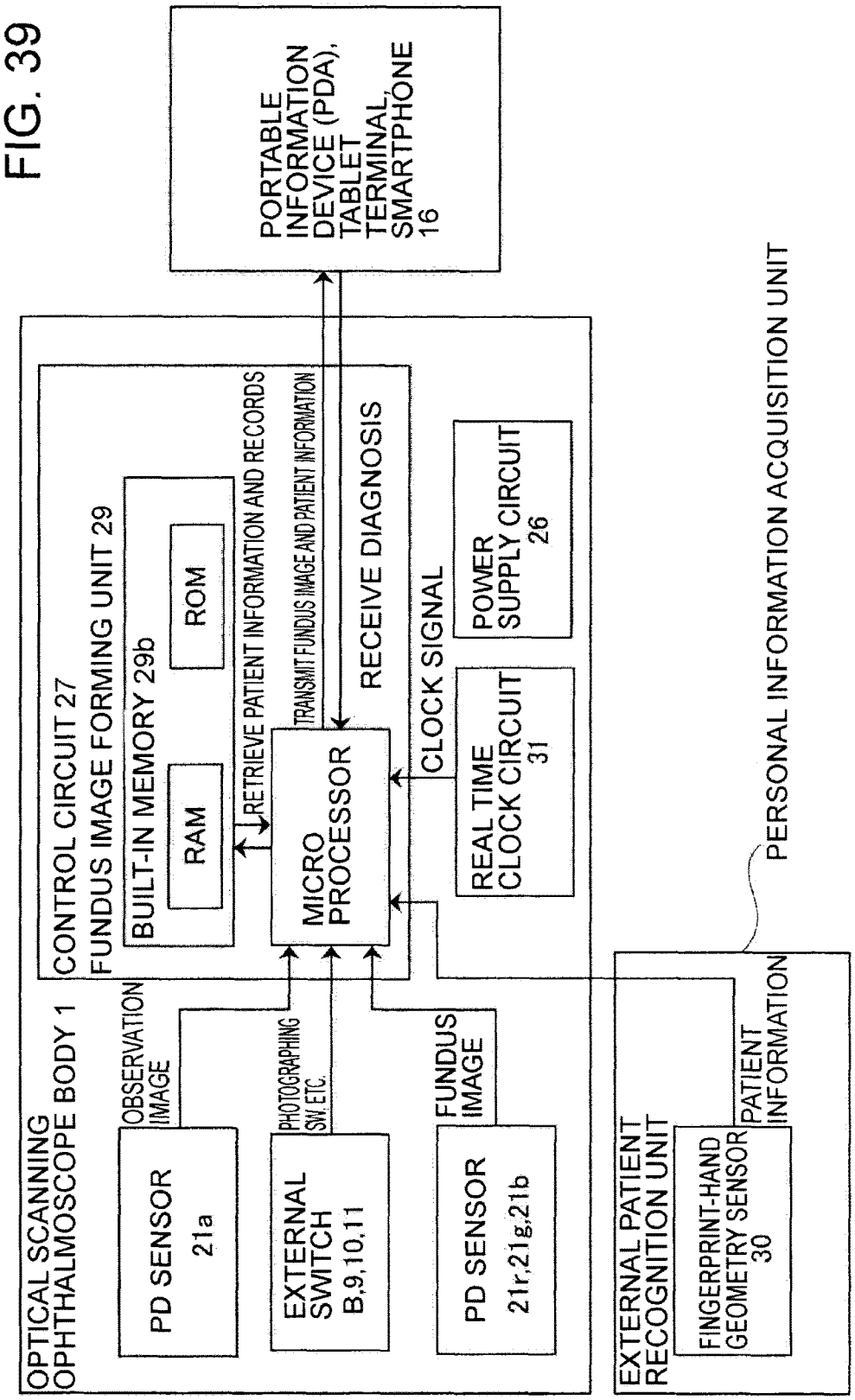
FIG. 39 is a schematic diagram illustrating an example of the configuration of a fundus imaging system according to an embodiment.

FIG. 39 illustrates a configuration example 1 of the fundus imaging system of this embodiment. In the configuration example 1, palm shape (hand geometry) or fingerprint recognition sensor is used as a personal information acquisition unit (external patient recognition unit). Note that applicable biometric authentication information in the configuration example 1 is not limited to the hand geometry and fingerprints. For example, a palm print or a pattern of hand or finger vein (blood vessel) may also be applicable.

A fingerprint-hand geometry sensor 30 is connected to the control circuit 27 of the optical scanning ophthalmoscope body 1. The ROM of the control circuit 27 stores a personal information acquisition control program for controlling the fingerprint-hand geometry sensor 30, and a program, as an association unit, for associating the personal information with a fundus image. The control circuit 27 includes a microprocessor. The microprocessor receives a clock signal from a real time clock circuit 31.

In this operation example, when the power button B is turned on, and a personal information acquisition control program load switch (not illustrated) is operated, the personal information acquisition control program is automatically loaded into the microprocessor of the control circuit 27. When the subject touches the fingerprint-hand geometry sensor 30 with his/her finger or hand, the fingerprint or handprint is acquired as personal information. The personal information thus acquired is stored in the RAM of a built-in memory 29b.

In the example described above, the operation mode is automatically switched to the observation mode in response to the acquisition of personal information. However, when the subject performs photographing on his/her own as in this operation example, the subject performs fundus photography by operating the photographing button 9 (external switch) without fundus observation. When fundus photography is performed, the fundus image EGr acquired and personal information obtained before the fundus photography are temporarily stored in RAM in association with each other.

The fundus image EGr and the personal information are sent to the portable information device 16' on the examiner's side as illustrated in FIG. 38 through the portable information device 16. In this manner, the medical institution on the examiner's side acquires the personal information and the fundus image obtained by the fundus photography performed by the subject.

CONFIGURATION EXAMPLE 2

Figure 40:
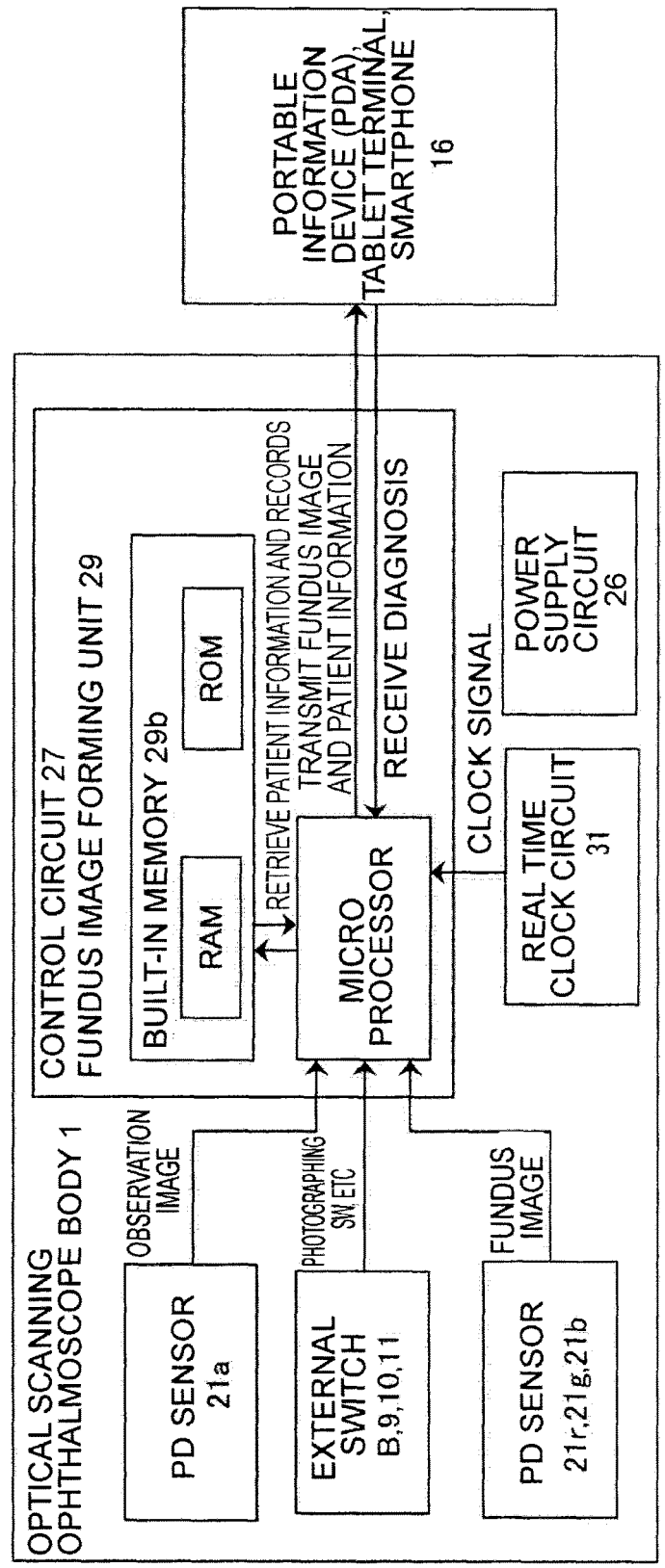
FIG. 40 is a schematic diagram illustrating an example of the configuration of a fundus imaging system according to an embodiment.

FIG. 40 illustrates a configuration example 2 of the fundus imaging system of this embodiment. In the configuration example 2, ROM stores a program for recognizing a retinal pattern or an iris pattern to acquire personal information.

To recognize a retinal pattern, when the power is turned on, a retinal pattern recognition program is loaded into the microprocessor. The scanning optical system illustrated in FIG. 37 is controlled by the retinal pattern recognition program. Thus, a retinal pattern image is acquired by the image processor 29a, and stored in the RAM.

Then, when the subject operates the photographing button 9, the fundus image EGr is acquired. The fundus image EGr is associated with retinal pattern image (personal information) and stored in the RAM. The fundus image EGr and the personal information are sent to the portable information device 16' on the examiner's side as illustrated in FIG. 38 through the portable information device 16. In this manner, the medical institution on the examiner's side acquires the personal information and the fundus image.

In the personal computer 16A, a retinal pattern image of each subject (each subject's eye) has been registered in advance. The personal computer 16A matches the retinal pattern image sent from the subject side against a retinal pattern image registered in advance to identify the subject.

To recognize an iris pattern, an iris pattern recognition program is loaded into the microprocessor. When the iris pattern recognition program has been loaded into the microprocessor, the control circuit 27 inserts the projection lens LL for the anterior segment photography illustrated in FIG. 37 in the optical path of the scanning optical system.

Next, the control circuit 27 controls the scanning optical system to scan the iris Rp. Thus, an iris pattern image is acquired by the image processor 29a. The iris pattern image is stored in the RAM. Thereafter, when the photographing button 9 is operated by the subject, the projection lens LL is retracted from the optical path of the scanning optical system, and the fundus image EGr is acquired. The fundus image EGr thus acquired is associated with the iris pattern image as personal information and stored in the RAM.

The fundus image EGr and the personal information are sent to the portable information device 16' on the examiner's side as illustrated in FIG. 38 through the portable information device 16. In this manner, the medical institution on the examiner's side acquires the personal information and the fundus image.

In the configuration example 2, personal information can be acquired by using the scanning optical system for photographing the fundus image. Thus, the personal information can be acquired without having to unnecessarily complicate the physical configuration of the personal information acquiring unit.

CONFIGURATION EXAMPLE 3

Figure 41:
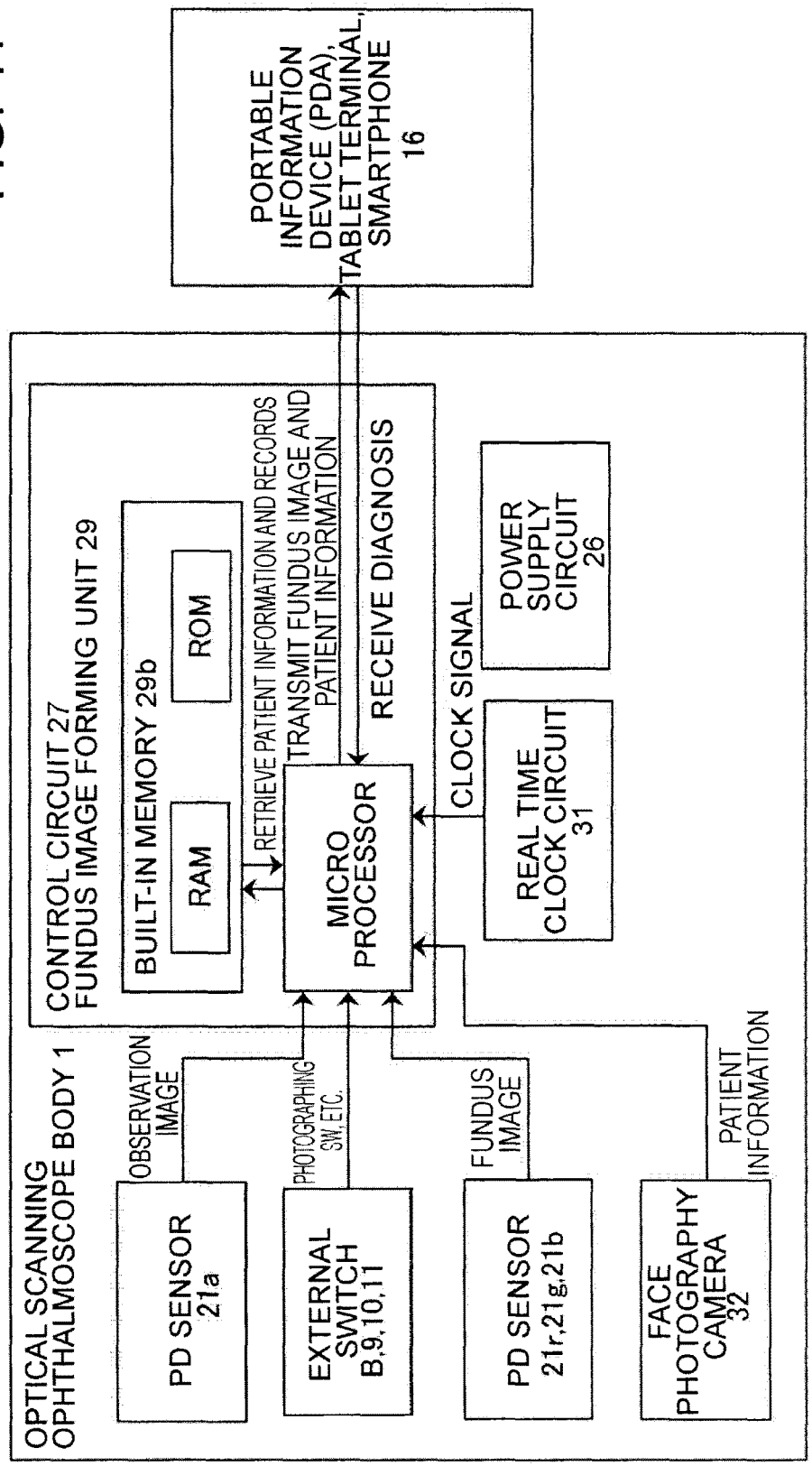
FIG. 41 is a schematic diagram illustrating an example of the configuration of a fundus imaging system according to an embodiment.

FIG. 41 illustrates a configuration example 3 of the fundus imaging system of this embodiment. In the configuration example 3, a face photographing camera 32 is provided for personal information acquisition. In this example, the face photographing camera 32 is configured to be actuated by an alignment button 10. When the alignment button 10 is operated, the face of the subject is photographed by the face photographing camera 32. Subsequent operations are the same as in the configuration examples 1 and 2, a detailed description thereof is omitted.

In the configuration example 3, a camera for face photography can be used for other processes than the personal information authentication such as determination on the brightness of photographing location.

The foregoing has described the configurations in which a fundus image is associated with personal information when the fundus is photographed by the subject himself/ herself. However, when the examiner attends the fundus photography, the same association process may be performed.

FOURTH EMBODIMENT

In the third embodiment, a description is given of the fundus imaging system using an optical scanning ophthalmoscope as the fundus imaging apparatus; however, the fundus imaging apparatus is not limited to the optical scanning ophthalmoscope. For example, an optical coherence tomography described in the background art may be employed as the fundus imaging apparatus.

Incidentally, if an optical coherence tomography is employed, the optical coherence tomography may be portable (accordingly, the configuration as illustrated in FIGS. 1 to 6 in the first embodiment can be applied). The optical coherence tomography may also be for both portable and stationary use, or stationary use only.

Figure 42:
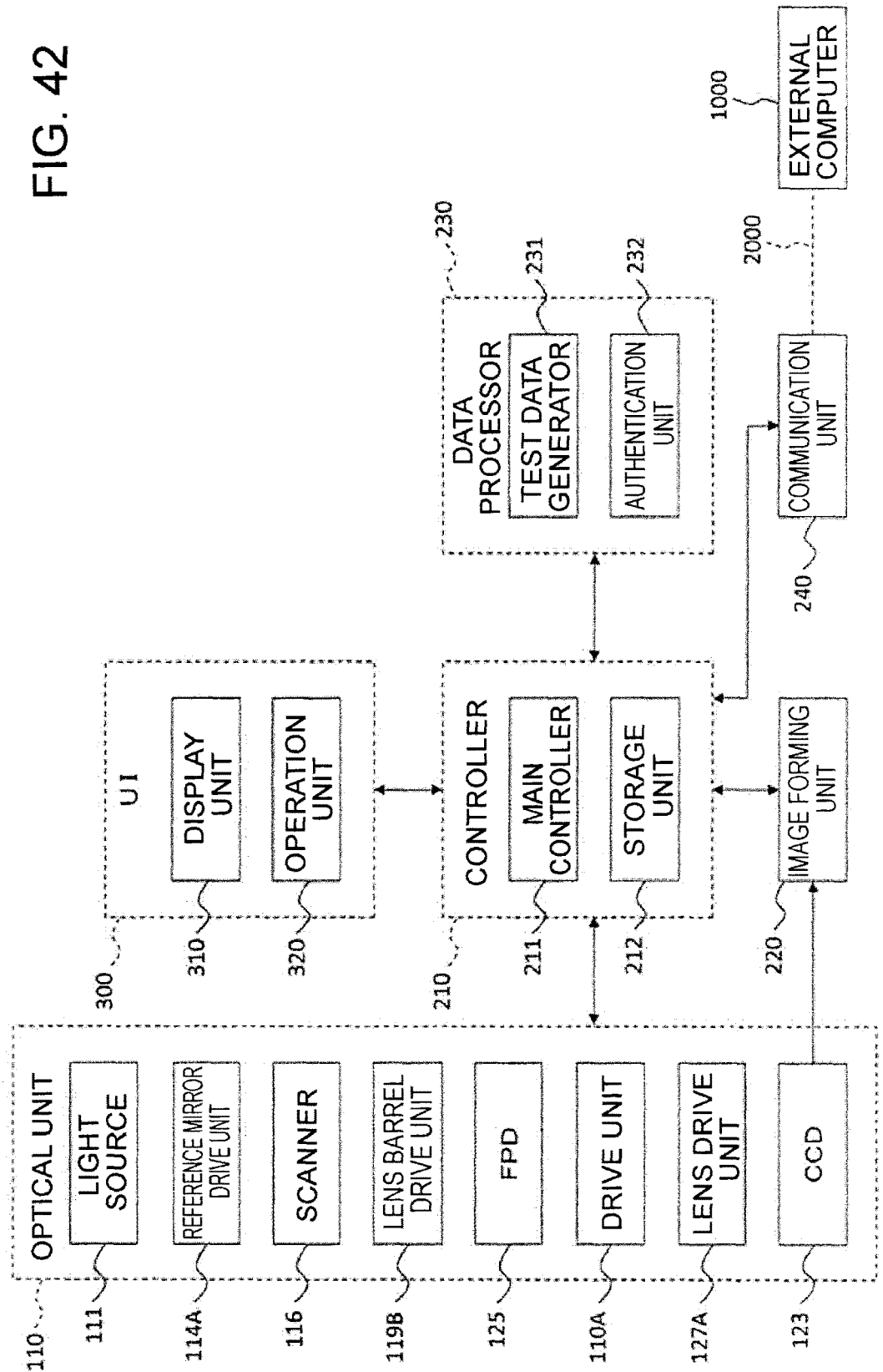
FIG. 42 is a schematic diagram illustrating an example of the configuration of a fundus imaging system according to an embodiment.

The optical coherence tomography of this embodiment has the same optical system as the second embodiment. The following description refers to FIG. 35 of the second embodiment as appropriate. The data processor 230 of the optical coherence tomography of this embodiment includes a test data generator 231 and an authentication unit 232 (see FIG. 42). The test data generator 231 generates test data. The test data is generated by processing the detection result of interference light by the optical unit 110 and indicates the state of the subject's eye (the details are described later). In this embodiment, the test data is used as authentication information to authenticate the subject. The storage unit 212 stores in advance the same setting information as described in the second embodiment and regular personal authentication information described below.

(Regular Personal Authentication Information)

The regular personal authentication information is personal authentication information to authenticate a person (authorized subject) who is allowed to have a test by using the fundus imaging apparatus 100. The personal authentication information is used for the personal authentication of a person who wishes to have a test using the fundus imaging apparatus 100. The personal authentication information is used as the personal information in the first embodiment.

The personal authentication information may be character string information or image information. Examples of the character string information include patient ID issued by the medical institution, personal information such as subject name, character string information arbitrarily designated by the subject, character string information randomly designated, and the like. Examples of the image information include biometric information (fingerprint pattern, iris pattern, vein pattern, face type pattern. etc.), a one-dimensional code, a two-dimensional code, and the like. In addition, a voice pattern and a handwriting pattern may also be used as the personal authentication information.

The personal authentication information may also be obtained based on images of the subject's eye E that can be acquired by the fundus imaging apparatus 100 (two-dimensional cross sectional image, three-dimensional image, fundus front image, etc.). Examples of such personal authentication information include the following: (1) morphological information indicating the morphology of a predetermined site of the fundus (blood vessel, optic papilla, layer tissue, laser treatment scar, etc.); (2) distribution information representing the distribution of a predetermined site of the fundus; (3) layer thickness distribution information indicating distribution of the thickness of a predetermined layer tissue of the fundus; (4) the distance between the fundus and the anterior segment (eye axial length, etc.). How to acquire the personal authentication information is described later.

The morphological information of blood vessels includes, for example, a blood vessel pattern, the number, thickness, length, and curvature of the blood vessels, the number of branches of the blood vessels, the number of intersections of the blood vessels. The distribution information of blood vessels includes, for example, the positions (distribution) of the blood vessels, the curvature distribution of the blood vessels, the positions of the bifurcations of the blood vessels, the positions of the intersections of the blood vessels. The morphological information of the optic papilla includes, for example, its shape and size (area, disc diameter, cup diameter, rim diameter, the ratio of these diameters, depth, etc.). The distribution information of the optic papilla includes, for example, its location. The morphological information of a layer tissue includes, for example, its shape and size (length, thickness). The distribution information of a layer tissue includes, for example, its location. The morphological information of a characteristic site (laser treatment scar, lesion, etc.) includes, for example, its shape and size. The distribution information of a characteristic site includes, for example, its location.

A person who wishes to have a test by using the fundus imaging apparatus 100 inputs personal authentication information in a predetermined manner. The input method corresponds to the type of personal authentication information to be used. The same personal authentication information as in the first embodiment is entered in the same manner as in the first embodiment. Besides, personal authentication information acquired via OCT measurement is entered by actually performing OCT measurement for the subject's eye E and processing an image obtained thereby.

When the fundus imaging apparatus 100 is shared by two or more subjects, regular personal authentication information for each subject is stored in the storage unit 212 in advance.

(Test Data Generator 231)

The test data generator 231 processes the detection result of interference light from the optical unit 110, and thereby generates test data indicating the state of the subject's eye E. The "detection result of interference light" is, for example, one of the following: (1) a signal output from the CCD image sensor 123; (2) image data formed by the image forming unit 220; (3) data obtained in the middle of the process performed by the image forming unit 220 (i.e., data obtained in the middle of the image data forming process); (4) data obtained by processing the signal output from the CCD image sensor 123 by a constituent element other than the image forming unit 220. The following illustrates examples of the process performed by the test data generator 231.

As a first example, the test data generator 231 may generate layer thickness information of the fundus Ef based on the detection result of interference light from the optical unit 110. In this case, the test data generator 231 functions as a layer thickness information generator and performs fundus layer thickness analysis (retinal thickness analysis, RNFL thickness analysis, etc.) as mentioned above. In addition, the test data generator 231 may perform the comparative analysis of a standard layer thickness value and layer thickness information obtained by the fundus layer thickness analysis.

The retinal layer thickness analysis is performed based on the detection result of interference light to find the thickness (distribution thereof) of a predetermined layer tissue of the fundus Ef. The retinal thickness analysis is explained as an example. The same process may also be performed to obtain the thickness of the other layer tissue.

In the retinal thickness analysis, for example, an OCT image of the fundus Ef (cross sectional image, three-dimensional image) is analyzed to obtain the thickness distribution of the retina in part or all of the scan area. Note that the retinal thickness has various definitions. For example, the retinal thickness may be defined as a thickness of up to the inner nuclear layer (inner segment/outer segment junction of photoreceptor cells) from the inner limiting membrane, a thickness from the inner limiting membrane to the retinal pigment epithelial layer, etc. The retinal thickness obtained by the retinal thickness analysis is one of such definitions.

For example, the retinal thickness analysis is performed in the following manner. First, an OCT image of the fundus Ef is analyzed to specify an image region corresponding to predetermined boundaries (e.g., the inner limiting membrane and the retinal pigment epithelial layer). Then, the number of pixels between the boundaries specified is counted to obtain the retinal thickness (the distance in the depth direction). For example, Japanese Unexamined Patent Application Publications No. 2007-325831, No. 2008-206684, No. 2009-61203, No. 2009-66015, etc. by the present applicant describes the process of analyzing an OCT image to obtain the thickness of fundus layers. The information thus acquired is an example of "layer thickness distribution information".

By the same process as the retinal thickness analysis, it is possible to specify an image region corresponding to an arbitrary layer tissue of the fundus Ef as well as to obtain the layer thickness distribution of the arbitrary layer tissue. Thereby, it is possible to acquire morphological information indicating the morphology of a predetermined site (a predetermined layer tissue) of the fundus Ef, distribution information representing the distribution of a predetermined site, and further, layer thickness distribution information of a predetermined layer tissue.

The comparative analysis of the retinal thickness is an analysis process to compare the retinal thickness obtained by the retinal thickness analysis with standard data (normative data) stored in advance. The normative data is a standard value of the retinal thickness of a healthy eye (standard thickness). The normative data is created by measuring a number of retinal thicknesses of healthy eyes and calculating a statistic (average value, standard deviation, etc.) of the measurement results. The comparative analysis determines whether the retinal thickness of the subject's eye E falls in the range of healthy eyes. The comparative analysis may be a process of determining whether the retinal thickness obtained by the retinal thickness analysis falls in a predetermined range of the retinal thickness of eyes with a disease.

The test data generator 231 may be configured to be capable of an analysis process for identifying an image region corresponding to a characteristic site (laser treatment scar, lesion, etc.) of the fundus Ef. This is an analysis process of, for example, analyzing an OCT image to obtain morphological information and/or distribution information of the characteristic site in part or all of the scan area.

The analysis process includes, for example, a process of specifying pixels corresponding to the characteristic site from among the pixels of the OCT image. As a specific example, pixels having pixel values belonging to a range predetermined according to the characteristic site may be specified. As another example, a histogram of pixel values may be created for the pixels that form the OCT image, and pixels corresponding to the characteristic site may be specified based on the distribution of pixel values in the histogram.

As still another example, the OCT image may be divided into a plurality of image regions, or a predetermined image region of the OCT image may be specified, and then pixels corresponding to the characteristic site may be specified based on the morphology of the image region. For example, an image region corresponding to Bruch's membrane and an image region corresponding to the retinal pigment epithelium may be specified, and an image region corresponding to a small substantially circular raised shape may be specified as (candidate for) drusen based on pixel values between these image regions. Processing of identifying image regions based on such a shape may include, for example, image matching using a template in the shape.

When the above-mentioned front image acquisition optical system is provided, and an image of the fundus Ef can be captured, an image region corresponding to a characteristic site may be specified based on the captured image of the fundus Ef. The analysis process is implemented by determining, for example, whether the pixel value of each pixel in the captured image falls in a predetermined range, and specifying pixels in the predetermined range. If the captured image is a color image, the characteristic site has a characteristic shape and/or color. Specifically, a laser treatment scar is depicted as a small round white spot, and a lesion is depicted in a characteristic color (e.g. drusen is yellowish white). Thus, by searching for an image region corresponding to such characteristic shape and/or color, an image region corresponding to the characteristic site can be specified. If the captured image is a monochrome image, by searching for an image region corresponding to a characteristic shape and/or brightness (luminance), an image region corresponding to the characteristic site can be specified.

The disc shape analysis may include the analysis process of detecting a hole in the retina by analyzing an OCT image of the fundus Ef, and obtaining the shape of the hole, that is, the shape of the optic disc. In the disc shape analysis, for example, a cross sectional image or a three-dimensional image is analyzed to specify an image region corresponding to the optic disc and the retinal surface in the vicinity thereof, and the specified image region is analyzed to obtain a parameter (disc shape parameter) representing the global or local shape (concave-convex). Examples of the disc shape parameter include the cup diameter, the disc diameter, the rim diameter, the papillary depth of the optic disc, and the like.

The disc shape analysis may include the analysis process of obtaining the slope of the optic disc (asymmetry of the shape). This analysis process is performed, for example, as follows. First, the test data generator 231 specifies the disc center by analyzing a three-dimensional image obtained by scanning an area including the optic disc. Then, the test data generator 231 sets a circular area around the disc center, and obtains a plurality of partial regions by radially dividing the circular area. Subsequently, the test data generator 231 analyzes the cross sectional image of the circular area, and obtains the height position of a predetermined layer (e.g., retinal pigment epithelial layer) at each pixel location. In addition, the test data generator 231 calculates the average value of the height positions of the predetermined layer in the partial regions. Next, the test data generator 231 compares a pair of average values obtained for a pair of partial regions corresponding to opposite positions with respect to the disc center, and obtains the inclination of the fundus Ef in the opposite directions. The test data generator 231 generates inclination distribution information indicating the distribution of the inclination of the fundus Ef in the circular area based on inclinations obtained for a plurality of opposite directions. Evaluation information on the state of disease may be generated based on the inclination distribution information (and information indicating standard distribution thereof).

A fundus front image may be formed based on a three-dimensional image acquired by OCT. The fundus front image is an image that is rendered on a plane perpendicular to the incident direction of measurement light (z direction) on the fundus Ef. The fundus front image is formed by projecting part or all of the three-dimensional image in the depth direction of the fundus Ef (z direction). This process is performed by the data processor 230. The fundus front image is referred to as a projection image.

If the fundus front image is formed by using only part of the three-dimensional image, the partial area may be a part in the xy direction or a part in the z direction. The former is applied to, for example, obtain a fundus front image of a predetermined site (the optic disc, macula, etc.). The latter is applied to, for example, obtain a fundus front image containing information of a predetermined area in the z direction. When part of the region in the z direction of the three-dimensional image is used, the top and/or bottom surface(s) of the partial region may be either plane or curved. Further, an image rendered in a plane at an arbitrary angle with respect to the z direction (inclined fundus image) may be formed based on the three-dimensional image.

The test data generator 231 may generate test data based on the fundus front image (or the inclined fundus image). The type of test data based on the fundus front image may be the same as that of test data based on other types of OCT images (two-dimensional cross sectional image, three-dimensional image, etc.) such as the morphological information, the distribution information, etc.

As described above, the data processor 230 can image any cross section of the three-dimensional image (MPR image). A cross section is designated manually or automatically. The test data generator 231 may generate test data based on the MPR image. The type of test data based on the MPR image may be the same as that of test data based on other types of OCT images such as the morphological information and the distribution information.

The test data generator 231 may find intraocular distance as test data. To obtain intraocular distance from a two-dimensional cross sectional image or a fundus front image, the test data generator 231 specifies a plurality of positions in the image. The positions specified are points of interest in the subject's eye E (disc center, fovea centralis, lesion, etc.), and are points specified manually by the user or obtained by image analysis.

The test data generator 231 is capable of specifying intraocular distance based on two or more OCT images. As an example, the process of obtaining the axial length is described below. The fundus imaging apparatus 100 can switch the operation mode between fundus mode to acquire an image of the fundus Ef and anterior segment mode for forming an image of the anterior segment. The operation mode is switched by inserting/retracting the switchable lens 127 in/from the measurement optical path. The switchable lens 127 and the lens drive unit 127A are an example of "mode switch unit". The main controller 211 stores, in the storage unit 212, position information of the reference mirror 114 applied in the fundus mode, and position information of the reference mirror 114 applied in the anterior segment mode. In the fundus mode, a two-dimensional cross sectional image or a three-dimensional image including the center position of the fundus surface is acquired. In the anterior segment mode, a two-dimensional cross sectional image or a three-dimensional image including the corneal vertex is acquired.

The test data generator 231 calculates the distance between, the fundus and the anterior segment based on an OCT image acquired in the fundus mode (fundus OCT image) and an OCT image acquired in the anterior segment mode (anterior segment OCT image). As a specific example, the test data generator 231 specifies the coordinates corresponding to the fundus center (fundus center coordinates) by analyzing the fundus OCT image as well as specifying the coordinates corresponding to the corneal vertex (cornea vertex coordinates) by analyzing the anterior segment OCT image. In addition, the test data generator 231 calculate the axial length of the subject's eye E based on the fundus center coordinates, the cornea vertex coordinates, the displacement of the focal point of measurement light due to switching of the operation mode, position information of the reference mirror 114 in both operation modes.

(Authentication Unit 232)

In this embodiment, test data obtained by the test data generator 231 may be used as personal authentication information. Besides, the storage unit 212 stores regular personal authentication information in advance. The authentication unit 232 matches the personal authentication information such as test data against the regular personal authentication information. The authentication unit 232 sends the authentication result (information indicating whether or not the authentication is successful) to the controller 210.

If the authentication is successful, the controller 210 controls the fundus imaging apparatus 100 to perform OCT measurement. On the other hand, if the authentication fails, the controller 210 displays predetermined notification information on the display unit 310, for example. The notification information includes a message indicating that the authentication has failed, a message prompting the user to reenter the personal authentication information, a message prompting the input of other personal authentication information, or the like.

Described below is the authentication process. When test data is used as personal authentication information, even if the test data is of an authenticated subject's eye, personal authentication information may not exactly match regular personal authentication information because of the presence of measurement error. Therefore, even if there is some degree of difference between the personal authentication information and the regular personal authentication information, it is required to determine that the two match successfully. As an example, an allowable range (a threshold, etc.) may be set in advance for the difference between the personal authentication information and the regular personal authentication information. The authentication unit 232 obtains the difference between the personal authentication information and the regular personal authentication information to determine whether this difference falls within the allowable range. If the difference is within the allowable range, the authentication unit 232 obtains an authentication result that the authentication is successful. On the other hand, if the difference is out of the allowable range, the authentication unit 232 obtains an authentication result that the authentication fails.

As mentioned above, there are various types of personal authentication information. Therefore, it is possible to selectively use a plurality of pieces of personal authentication information. In the following, a description is given of a case where two pieces of personal authentication information are used.

The storage unit 212 stores in advance regular personal authentication information related to first personal authentication information (first regular personal authentication information), and regular personal authentication information related to second person authentication information (second regular personal authentication information).

It is assumed that the first personal authentication information is acquired first. The authentication unit 232 matches the acquired first personal authentication information against the first regular personal authentication information. If the authentication is successful, imaging by the fundus imaging apparatus 100 is allowed. On the other hand, if the authentication fails, then the second personal authentication information is acquired. The authentication unit 232 matches the acquired second personal authentication information against the second regular personal authentication information. If the authentication is successful, imaging by the fundus imaging apparatus 100 is allowed. On the other hand, if the authentication fails, the controller 210 displays on the display unit 310 notification information including a message indicating that the authentication has failed, a message prompting the user to reenter the personal authentication information, a message prompting the input of other personal authentication information, or the like.

When two or more subjects share the fundus imaging apparatus 100, that is, when there are two or more regular subjects, the storage unit 212 stores regular personal authentication information for each of the subjects. When personal authentication information is acquired, the controller 210 sends all the regular personal authentication information stored in the storage unit 212 to the authentication unit 232.

The authentication unit 232 matches the acquired personal authentication information against the regular personal authentication information. If the acquired personal authentication information matches one of the regular personal authentication information, a subject corresponding to this regular personal authentication information is recognized as the subject of this test. On the other hand, when the acquired personal authentication information do not match any of the regular personal authentication information, the controller 210 displays on the display unit 310 notification information as described above.

(Association Process)

The personal authentication information generated by the test data generator 231 is sent to the controller 210, and is stored in the storage unit 212. An OCT image formed by the image forming unit 220 (and the data processor 230) is sent to the controller 210, and is stored in the storage unit 212. The controller 210 associates the OCT image with the personal authentication information (personal information).

This process is performed in the same manner as in the first embodiment. The controller 210 is an example of "association unit".

(Communication Unit 240)

The communication unit 240 sends an OCT image and the personal authentication information (personal information) associated with each other by the controller 210 to the external computer 1000. The communication unit 240 is an example of "transmitter".

[Operation and Effects]

Described below are the operation and effects of the fundus imaging system according to the embodiment.

The fundus imaging system of this embodiment includes a fundus imaging apparatus (100), a personal information acquisition unit (the test data generator 231), and an association unit (the controller 210). The fundus imaging apparatus is configured to capture an image of the fundus of a subject's eye. The personal information acquisition unit is configured to acquire personal information of the subject. The association unit is configured to associate the image of the fundus captured by the fundus imaging apparatus with the personal information acquired by the personal information acquisition unit.

According to the embodiment, each fundus image can be automatically associated with personal information. Thus, the fundus image can be easily associated with the personal information. For example, the association can be made even if test is performed without the attendance of an examiner.

The fundus imaging apparatus of this embodiment may include a transmitter (the communication unit 240) that transmits an image associated with personal information by the association unit. With this configuration, an image and personal information associated with each other can be sent to an external device.

The fundus imaging apparatus of this embodiment may include an optical system and a processor as follows. The optical system scans the fundus of the subject's eye with measurement light, and detects interference light obtained by superposing reference light on return light of the measurement light from the fundus. In other words, the optical system is an interference optical system for performing OCT (see FIG. 35). The processor forms a fundus image by processing the detection result of interference light by the optical system. In this embodiment, the processor includes at least the image forming unit 220, and may include the data processor 230. In addition, the personal information acquisition unit (the test data generator 231) acquires personal information (personal authentication information) based on the image formed by the processor.

With this configuration, personal information can be acquired based on an OCT image. In particular, it is possible to acquire personal information that reflects the morphology and/or distribution of the fundus in the depth direction, and further the three-dimensional morphology and/or distribution of a site of the fundus. In addition, it is possible to use, as personal information, function information (blood flow information, etc.) obtained by a functional OCT such as Doppler OCT.

In this embodiment, the personal information acquisition unit (the test data generator 231) may be configured to analyze an image formed by the processor to acquire one or both of the following pieces of personal information: morphological information representing the morphology of a predetermined site of the fundus; distribution information representing the distribution of a predetermined site of the fundus. The predetermined site of the fundus may include any of fundus blood vessel, optic disc, predetermined layer tissue, and laser treatment scar.

This embodiment may employ a configuration including the following: an optical system configured to scan a three-dimensional region of the fundus with measurement light; a processor configured to form a three-dimensional image of the fundus; and a personal information acquisition unit configured to acquire personal information based on the three-dimensional image. With this configuration, personal information can be acquired based on a three-dimensional image having a large amount of information. For example, with respect to a predetermined site of the fundus, it is possible to obtain two-dimensional morphology or three-dimensional morphology as well as two-dimensional distribution or three-dimensional distribution. This configuration increases the degree of freedom of personal information to be acquired.

This embodiment may also employ a configuration including the following: an optical system configured to scan a three-dimensional region of the fundus with measurement light; a processor configured to form a three-dimensional image of the fundus; the processor configured to project at least a part of the three-dimensional image in the depth direction of the fundus to form a fundus front image (projection image); and a personal information acquisition unit configured to acquire personal information based on the fundus front image. The fundus front image includes information on an area that has been subjected to the projection process. This configuration increases the degree of freedom of personal information to be acquired.

This embodiment may also employ a configuration including the following: an optical system configured to scan a three-dimensional region of the fundus with measurement light; a processor configured to form a three-dimensional image of the fundus; the processor configured to form a two-dimensional cross sectional image representing a cross section of the three-dimensional image; and a personal information acquisition unit configured to acquire personal information based on the two-dimensional cross sectional image. With this configuration, personal information can be acquired based on an image representing an arbitrary cross section of the fundus. Further, this configuration increases the degree of freedom of personal information to be acquired.

In this embodiment, the personal information acquisition unit may be configured to analyze an image formed by the processor, and thereby acquire layer thickness distribution information representing the distribution of the thickness of a predetermined layer tissue of the fundus. The layer thickness distribution information may be used as personal information.

In this embodiment, the fundus imaging apparatus may include a mode switch unit (the switchable lens 127 and the lens drive unit 127A) configured to switch operation modes between fundus mode for forming an image of the fundus of the subject's eye and anterior segment mode for forming an image of the anterior segment of the subject's eye. In this case, the personal information acquisition unit can calculate the distance between the fundus and the anterior segment based on a fundus image formed in the fundus mode and an anterior segment image formed in the anterior segment mode. The distance may be used as personal information.

Note that the mode switch unit need not necessarily be configured to insert/retract the switchable lens in/from the optical path of measurement light. For example, the fundus mode and the anterior segment mode may be switched with a configuration capable of changing the length of the optical path of reference light by a sufficient distance. As a specific example, the reference mirror (114) may be configured to be movable in a range obtained by adding a predetermined distance to the general length of the eye's axis.

The fundus imaging system of this embodiment may include a storage unit and a matching unit as follows. The storage unit (the storage unit 212) stores in advance regular personal authentication information for an authorized subject who is allowed to perform imaging by using the fundus imaging apparatus. The matching unit matches personal information acquired by the personal information acquisition unit against the regular personal authentication information. The fundus imaging apparatus performs imaging when the personal information matches the regular personal authentication information in the matching unit. Such a configuration may be applied to the first embodiment. With this configuration, each subject can be authenticated to determine whether he/she is allowed to use the system.

In the above example, while the fundus imaging apparatus is provided with a storage unit, the storage unit may be provided to a device connected to the fundus imaging apparatus. For example, the storage unit may be provided in a server or a network-attached storage (NAS).

In this embodiment, the matching unit may be configured to determine that the authentication is successful when the difference between the personal information and the regular personal authentication information falls within an allowable range set in advance. With this configuration, personal authentication can be suitably performed using biometric information.

This embodiment may employ the following configuration: if the difference between the personal information and the regular personal authentication information is not within the predetermined allowable range, the personal information acquisition unit acquires other personal information; and the matching unit matches the acquired other personal information against other regular personal authentication information stored in the storage unit in advance. With this configuration, when the authentication has failed for one type of personal information, another authentication can be performed by using another type of personal information. Thus, authentication can be suitably performed using, for example, biometric information.

In this embodiment, the fundus imaging apparatus may be portable and/or stationary. This increases the degree of freedom of the system configuration.

FIFTH EMBODIMENT

This embodiment describes a fundus imaging system capable of acquiring a plurality of types of personal information. The types of personal information may include any one or more of personal information used in the third and the fourth embodiments. The following is described based on the fourth embodiment.

FIRST CONFIGURATION EXAMPLE

Figure 43:
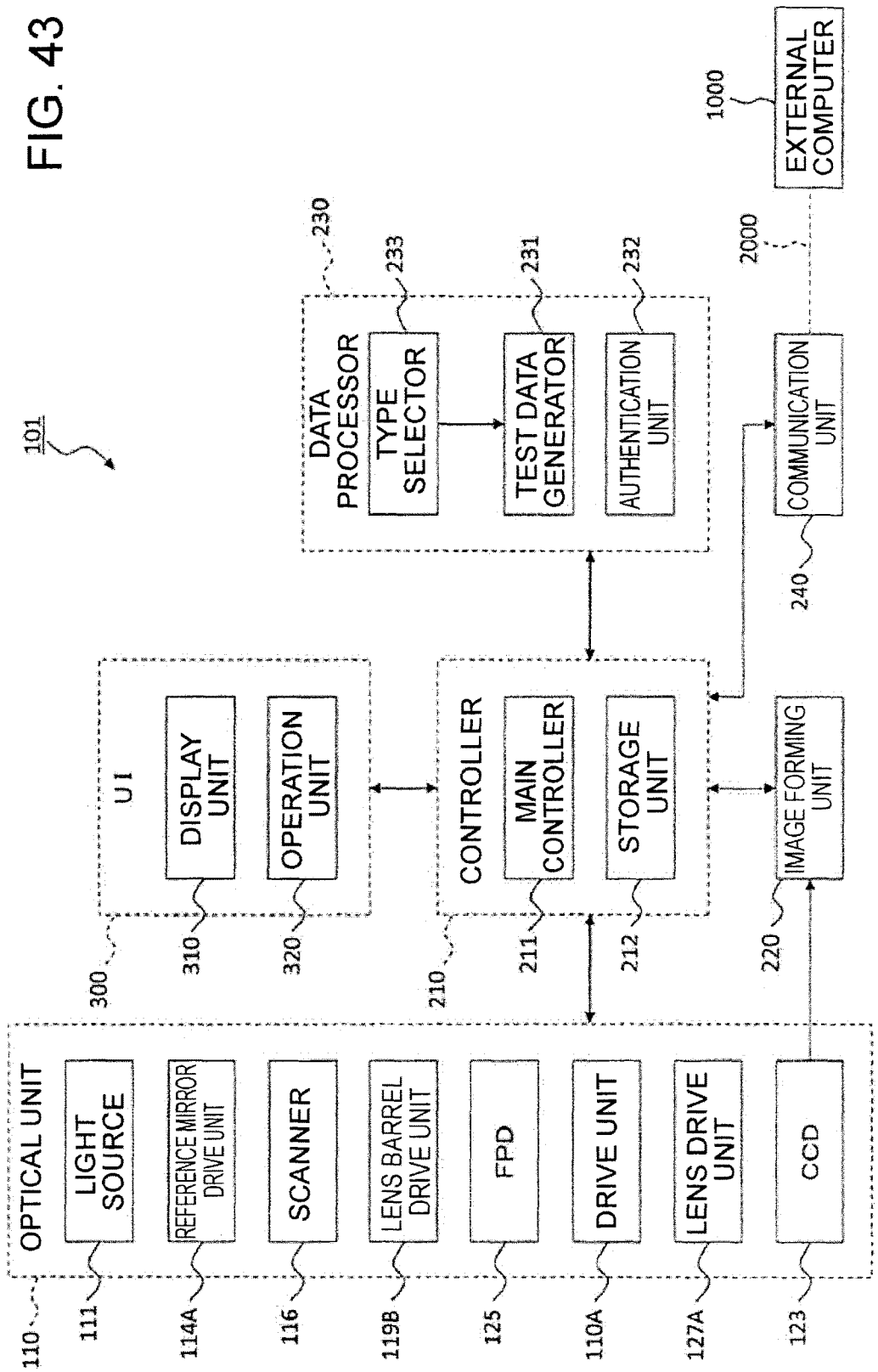
FIG. 43 is a schematic diagram illustrating an example of the configuration of a fundus imaging system according to an embodiment.

FIG. 43 illustrates a configuration of a fundus imaging apparatus in a fundus imaging system of this example. A fundus imaging apparatus 101 has a function for inputting medical history of a subject. The medical history is information indicating the contents of medical care provided in the past for the subject. The medical history includes history of disease, history of treatment, history of medication, and the like. The medical history is entered by, for example, acquiring the electronic medical records of the subject through a network, or manual input by the user. The former is performed by, for example, the communication unit 240 under the control of the controller 210. The latter is performed on, for example, a predetermined input screen displayed on the display unit 310 via the operation unit 320. These are an example of "medical history input unit".

The data processor 230 of the fundus imaging apparatus 101 further includes a type selector 233. The type selector 233 selects one or more types from among a plurality of types of personal information based on the medical history entered. Here, the "plurality of types" are set in advance, and are, for example, all types of personal information that can be acquired by the personal information acquisition unit (the test data generator 231, etc.). Further, part of the all types may be the "plurality of types". In this case, "the types" are set automatically or manually in advance.

Described below is an example of the type selector 233. The type selector 233 stores in advance association information that associates items contained in medical histories with the types of personal information. The items include, for example, disease name, drug name, treatment items, and the like. One or more types of personal information are associated with each item or a combination of two or more items. As a specific example, a certain item is associated with a type of personal information having a small effect (or no effect) on this item. For example, a macular disease is associated with morphological information related to an optic disc. On the other hand, an optic disc disease is associated with morphological information related to a macula. Besides, glaucoma is associated with distribution information of drusen related to age-related macular degeneration. Further, a disease without a change in axial length of an eye is associated with axial length of an eye.

The test data generator 231 is fed with information indicating the selection result by the type selector 233. For example, the test data generator 231 analyzes an OCT image to obtain personal information of the type selected by the type selector 233.

Described below are the effects of the fundus imaging system in this example. The personal information acquisition unit of this example is configured to be capable of acquiring a plurality of types of personal information.

The personal information acquisition unit of this example includes a medical history input unit and a type selector. The medical history input unit operates to receive the input of the medical history of the subject. The medical history input unit includes, for example, the controller 210 and the communication unit 240, or the user interface 300. Based on the medical history entered through the medical history input unit, the type selector (233) selects one or more types from among a plurality of types set in advance for personal information. The personal information acquisition unit operates to acquire personal information of the type selected by the type selector.

Incidentally, the personal information acquisition unit of the embodiment includes, for example, the data processor 230 (the test data generator 231 and the type selector 233) in addition to the medical history input unit (the controller 210 and the communication unit 240, or the user interface 300). Further, regarding the association unit and the transmitter, the configuration of the third embodiment or the fourth embodiment may be applicable.

With this fundus imaging system, it is possible to selectively apply personal information of a type corresponding to the medical history of the subject.

SECOND CONFIGURATION EXAMPLE

A fundus imaging apparatus in a fundus imaging system of this example has a configuration similar to the first configuration example (see FIG. 43). The fundus imaging apparatus has a function of acquiring the elapsed time since the last imaging of the fundus Ef of the subject's eye E. This function includes, for example, a first function of acquiring the electronic medical records of the subject via the network, a second function of acquiring the last imaging date from the electronic medical records, and a third function of calculating the elapsed time based on the imaging date (and time) and the current date (and time). The first function is implemented by, for example, the communication unit 240 under the control of the controller 210. The second and third functions are realized by the controller 210, for example. They are an example of "imaging interval acquisition unit".

In addition, the type selector 233 of this example selects one or more types from among a plurality of types of personal information based on the elapsed time fed by the imaging interval acquisition unit. This process is performed with reference to association information similar to the first configuration example, for example.

In the association information of this example, elapsed time is associated with types of personal information. Such association is determined according to, for example, the degree of chronological change of the personal information. Specifically, personal information are classified into: those that change over time such as morphological information and distribution information generated from a fundus image; and those that do not change over time such as character string information and fingerprint patterns. Besides, although the acquisition of the morphological information and the distribution information does not trouble the subject, the acquisition of the character string information and the fingerprint pattern is necessitated to trouble the subject. In consideration of this, it is possible to use personal information that changes over time when the elapsed time is short, and use personal information that does not change over time when the elapsed time is long. In addition, various types of personal information that changes over time may be classified according to factors such as the speed of chronological change and the accuracy of authentication, and associated arbitrarily with a time axis indicating the elapsed time.

If the selection result by the type selector 233 includes personal information based on an image of a fundus, the test data generator 231 is fed with information indicating the type of the personal information. For example, the test data generator 231 obtains personal information of the type selected by the type selector 233 by analyzing an OCT image.

Further, if the selection result by the type selector 233 includes personal information involving work by the subject, the controller 210 is fed with information indicating the type of the personal information. For example, the controller 210 displays, on the display unit 310, a message that promotes the user to perform a work for obtaining personal information of the type selected by the type selector 233.

Described below are the effects of the fundus imaging system in this example. The personal information acquisition unit of this example is configured to be capable of acquiring a plurality of types of personal information.

The personal information acquisition unit of this example includes an imaging interval acquisition unit and a type selector. The imaging interval acquisition unit acquires the elapsed time from the last imaging of the fundus. The imaging interval acquisition unit includes, for example, the controller 210 and the communication unit 240. The type selector (233) selects one or more types from among a plurality of types of personal information set in advance based on the elapsed time obtained by the imaging interval acquisition unit. The personal information acquisition unit operates to acquire personal information of the type selected by the type selector.

Incidentally, the personal information acquisition unit of the embodiment includes, for example, the data processor 230 (the test data generator 231 and the type selector 233, or the fingerprint-hand geometry sensor 30 of the third embodiment, etc.) in addition to the imaging interval acquisition unit (the controller 210 and the communication unit 240). Further, regarding the association unit and the transmitter, the configuration of the third embodiment or the fourth embodiment may be applicable.

With this fundus imaging system, it is possible to selectively apply personal information of a type corresponding to the elapsed time since the last imaging.

THIRD CONFIGURATION EXAMPLE

FIG. 44 illustrates a configuration of a fundus imaging apparatus in a fundus imaging system of this example. A fundus imaging apparatus 102 includes a candidate disease specifying unit 234 configured to analyze an image formed by the image forming unit 220 or the data processor 230, and thereby specify a candidate disease for the subject's eye E. The candidate disease refers to a disease that the subject's eye E may be suffering from. The image analysis performed by the candidate disease specifying unit 234 includes an arbitrary process for specifying a candidate disease (which may be a known process), and may include, for example, fundus layer thickness analysis, disc shape analysis, drusen analysis, etc. The candidate disease specifying unit 234 may be provided in the test data generator 231.

The data processor 230 of the fundus imaging apparatus 102 is provided with the type selector 233. The type selector 233 selects one or more types from among a plurality of types of personal information based on the candidate disease specified by the candidate disease specifying unit 234. This process is performed with reference to association information similar to the first configuration example, for example.

In the association information of this example, candidate diseases are associated with types of personal information. This association is achieved by, for example, associating one candidate disease with a type of personal information related to a site having a small effect (or no effect) of the candidate disease. As specific examples, a macular disease is associated with morphological information related to an optic disc. On the other hand, an optic disc disease is associated with morphological information related to a macula. Besides, glaucoma is associated with distribution information of drusen related to age-related macular degeneration. Further, a disease without a change in axial length of an eye is associated with axial length of an eye.

The test data generator 231 is fed with information indicating the selection result by the type selector 233. For example, the test data generator 231 analyzes an OCT image to obtain personal information of the type selected by the type selector 233.

Described below are the effects of the fundus imaging system in this example. The personal information acquisition unit of this example is configured to be capable of acquiring a plurality of types of personal information.

The personal information acquisition unit of this example includes a candidate disease specifying unit (234) and a type selector (233). The candidate disease specifying unit analyzes an image obtained by the fundus imaging apparatus (102), and thereby specifies a candidate disease of the subject's eye. The type selector selects one or more types from among a plurality of types set in advance for personal information based on the candidate disease specified by candidate disease specifying unit. The personal information acquisition unit operates to acquire personal information of the type selected by the type selector.

Incidentally, the personal information acquisition unit of the embodiment includes, for example, the data processor 230 (the test data generator 231 and the type selector 233) in addition to the candidate disease specifying unit (234). Further, regarding the association unit and the transmitter, the configuration of the third embodiment or the fourth embodiment may be applicable.

With this fundus imaging system, it is possible to selectively apply personal information of a type corresponding to a candidate diseases specified based on a fundus image.

[Modifications]

The embodiments described above are mere examples for embodying or carrying out the present invention, and therefore susceptible to several modifications and variations (omission, substitution, addition, etc.), all coming within the scope of the invention.

In the fifth embodiment, types of personal information are selectively used according to medical history, imaging interval, or candidate disease; however, it may be configured to change the allowable range in the matching process of the fourth embodiment.

While the above embodiments have described an optical scanning ophthalmoscope or an optical coherence tomography, a multi-functional product capable of applying a plurality of imaging modalities may be used as the fundus imaging apparatus. Examples of such multi-functional products include a device formed of a combination of an optical scanning ophthalmoscope and an optical coherence tomography, a device formed of a combination of a retinal camera and an optical coherence tomography, a device formed of a combination of an optical coherence tomography and a slit lamp microscope, a device formed of a combination of an optical scanning ophthalmoscope and a retinal camera, and the like. The multi-functional product performs a process of interest by any function arbitrarily. For example, the device formed of a combination of an optical scanning ophthalmoscope and an optical coherence tomography may be configured such that an alignment indicator is formed by the former, and a focus indicator is formed by the latter.

In the first and the second embodiments, light for imaging the fundus (light spot, measurement light, etc.) is used to form indicators; however, this light may be used for other applications. For example, this light may be used to apply a light stimulus to photoreceptor cells. Incidentally, light is irradiated to the same position of the fundus for a longer time to apply a light stimulus compared to when imaging is performed. Thus, the light source may be controlled to reduce the amount of light to apply a light stimulus to be smaller than that to perform imaging. Further, if the device formed of a combination of an optical scanning ophthalmoscope and an optical coherence tomography is used, imaging may be performed by the former (or the later) while a light stimulus may be applied by the latter (or the former).

A computer program for realizing the aforementioned embodiments may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (a hard disk, a floppy (registered trade mark) disk, ZIP, etc.), and the like.

The program may be transmitted/received through a network such as the Internet or LAN.

[Note]

Regarding the fundus imaging systems according to the third to fifth embodiments, notes are provided as follows.

In the population screening, home care, rural health care, retirement homes, and the like, a test (an examination) may be sometimes conducted without the attendance of an examiner. Under such test conditions, the examiner cannot specify a subject, and therefore it is desirable that the subject can easily associate fundus imaging or a fundus image with himself/herself (personal information).

In view of such circumstances, the third to fifth embodiments are intended to facilitate associating a fundus image with personal information. To achieve this object, the fundus imaging system is characterized as follows.

[Note 1]

A fundus imaging system including:

a fundus imaging apparatus configured to capture an image of a fundus of a subject's eye;

a personal information acquisition unit configured to acquire personal information of the subject, and an association unit configured to associate the image of the fundus captured by the fundus imaging apparatus with the personal information acquired by the personal information acquisition unit.

[Note 2]

The fundus imaging system as set forth in Note 1, further including a transmitter configured to transmit the image and the personal information associated with each other by the association unit.

[Note 3]

The fundus imaging system as set forth in Note 1 or 2, wherein the personal information acquisition unit is configured to acquire a retinal pattern of the subject as the personal information.

[Note 4]

The fundus imaging system as set forth in Note 3, wherein the fundus imaging apparatus includes:

a scanning optical system configured to scan the fundus of the subject's eye with a light spot, and receive return light of the light spot from the fundus by a light receiver;

a control circuit configured to control the scanning optical system such that a scanning locus is formed by the light spot in the fundus; and an image forming unit configured to form an image by the return light based on a light receiving signal from the light receiver and a position of the scanning locus, and the personal information acquisition unit is configured to acquire the retinal pattern using the image formed by the image forming unit.

[Note 5]

The fundus imaging system as set forth in Note 1 or 2, wherein the personal information acquisition unit is configured to acquire an iris pattern of the subject as the personal information.

[Note 6]

The fundus imaging system as set forth in Note 5, wherein the fundus imaging apparatus includes:

a scanning optical system configured to scan the fundus of the subject's eye with a light spot, and receive return light of the light spot from the fundus by a light receiver;

a control circuit configured to control the scanning optical system such that a scanning locus is formed by the light spot in the fundus;

an image forming unit configured to form an image by the return light based on a light receiving signal from the light receiver and a position of the scanning locus; and a projection lens configured to be inserted in/retracted from an optical path of the scanning optical system and project the light spot on an anterior segment of the subject's eye, and the personal information acquisition unit is configured to acquire the iris pattern using an image of the anterior segment formed by the image forming unit.

[Note 7]

The fundus imaging system as set forth in Note 1 or 2, wherein the personal information acquisition unit includes a face photographing camera configured to capture an image of the subject's face, and the personal information acquisition unit is configured to acquire the personal information using a face photograph captured by the face photographing camera.

[Note 8]

The fundus imaging system as set forth in Note 1 or 2, wherein the personal information acquisition unit is configured to acquire any one of a hand geometry, a fingerprint, a palm print, and a vein pattern of the subject as the personal information.

[Note 9]

The fundus imaging system as set forth in Note 1 or 2, wherein the fundus imaging apparatus includes:

an optical system configured to scan the fundus with measurement light and detect interference light obtained by superposing reference light on return light of the measurement light from the fundus; and a processor configured to form an image of the fundus by processing a detection result of the interference light obtained by the optical system, and the personal information acquisition unit is configured to acquire the personal information based on the image formed by the processor.

[Note 10]

The fundus imaging system as set forth in Note 9, wherein the personal information acquisition unit is configured to analyze the image formed by the processor to acquire morphological information indicating morphology of a predetermined site of the fundus and/or distribution information representing distribution of the predetermined site as the personal information.

[Note 11]

The fundus imaging system as set forth in Note 10, wherein the predetermined site includes any one of a blood vessel in the fundus, an optic disc, a predetermined layer tissue, and a laser treatment scar.

[Note 12]

The fundus imaging system as set forth in any one of Notes 9 to 11, wherein the optical system is configured to scan a three-dimensional region of the fundus with the measurement light, the processor is configured to form a three-dimensional image of the fundus, and the personal information acquisition unit is configured to acquire the personal information based on the three-dimensional image.

[Note 13]

The fundus imaging system as set forth in any one of Notes 9 to 11, wherein the optical system is configured to scan a three-dimensional region of the fundus with the measurement light, the processor is configured to form a three-dimensional image of the fundus, and form a fundus front image by projecting at least part of the three-dimensional image in depth direction of the fundus, and the personal information acquisition unit is configured to acquire the personal information based on the fundus front image.

[Note 14]

The fundus imaging system as set forth in any one of Notes 9 to 11, wherein the optical system is configured to scan a three-dimensional region of the fundus with the measurement light, the processor is configured to form a three-dimensional image of the fundus, and form a two-dimensional cross sectional image representing a cross section of the three-dimensional image, and the personal information acquisition unit is configured to acquire the personal information based on the two-dimensional cross sectional image.

[Note 15]

The fundus imaging system as set forth in Note 9, wherein the personal information acquisition unit is configured to analyze the image formed by the processor to acquire layer thickness distribution information indicating distribution of thickness of a predetermined layer tissue of the fundus as the personal information.

[Note 16]

The fundus imaging system as set forth in Note 9, wherein the fundus imaging apparatus includes a mode switch unit configured to switch operation mode between fundus mode for forming an image of the fundus of the subject's eye and anterior segment mode for forming an image of an anterior segment, and the personal information acquisition unit is configured to obtain a distance between the fundus and the anterior segment as the personal information based on the image of the fundus formed in the fundus mode and the image of the anterior segment formed in the anterior segment mode.

[Note 17]

The fundus imaging system as set forth in any one of Notes 1 to 16, wherein the personal information acquisition unit is configured to be capable of acquiring a plurality of types of personal information.

[Note 18]

The fundus imaging system as set forth in Note 17, wherein the personal information acquisition unit includes:

a medical history input unit configured to input medical history of the subject; and a type selector configured to select one or more types from among the plurality of types of personal information based on the medical history input by the medical history input unit, and the personal information acquisition unit is configured to acquire personal information of a type selected by the type selector.

[Note 19]

The fundus imaging system as set forth in Note 17, wherein the personal information acquisition unit includes:

an imaging interval acquisition unit configured to acquire an elapsed time since last imaging of the fundus; and a type selector configured to select one or more types from among the plurality of types of personal information based on the elapsed time acquired by the imaging interval acquisition unit, and the personal information acquisition unit is configured to acquire personal information of a type selected by the type selector.

[Note 20]

The fundus imaging system as set forth in Note 17, wherein the personal information acquisition unit includes:
a candidate disease specifying unit configured to analyze the image captured by the fundus imaging apparatus to specify a candidate disease for the subject's eye; and
a type selector configured to select one or more types from among the plurality of types of personal information based on the candidate disease specified by the candidate disease specifying unit, and the personal information acquisition unit is configured to acquire personal information of a type selected by the type selector.

[Note 21]

The fundus imaging system as set forth in any one of Notes 1 to 20, further including:
a storage configured to store in advance regular personal authentication information for an authorized subject who is allowed to perform imaging by using the fundus imaging apparatus; and
a matching unit configured to match the personal information acquired by the personal information acquisition unit against the regular personal authentication information, and
the fundus imaging apparatus is configured to perform imaging when the personal information matches the regular personal authentication information in the matching unit.

[Note 22]

The fundus imaging system as set forth in Note 21, wherein the matching unit is configured to determine that authentication is successful when a difference between the personal information and the regular personal authentication information falls within an allowable range set in advance.

[Note 23]

The fundus imaging system as set forth in Note 21, wherein
if the difference is out of the allowable range, the personal information acquisition unit acquires other personal information, and
the matching unit matches the other personal information against other regular personal authentication information stored in the storage in advance.

[Note 24]

The fundus imaging system as set forth in any one of Notes 1 to 23, wherein the fundus imaging apparatus is configured to be portable.

The invention claimed is:

1. A fundus imaging apparatus comprising:
a scanning optic that scans a fundus of a subject's eye with light from a light source, and receives return light from the fundus by a light receiver;
a microprocessor that is configured to control the scanning optic such that a scanning locus is formed by the light in the fundus; and
image forming circuitry that forms an image of the fundus based on a light receiving signal from the light receiver and a position of the scanning locus,
wherein the microprocessor is further configured to:
have operation modes including an alignment mode, in which the microprocessor is configured to control the scanning optic to project alignment indicators for aligning the scanning optic with the subject's eye on the fundus based on the light from the light source so that a plurality of alignment indicators are formed in different positions on the fundus;
determine a state of alignment based on the image of the fundus formed by the image forming circuitry and corresponding to the scanning locus formed on the fundus;
determine that the scanning optic is misaligned with respect to the subject's eye when at least one of the plurality of alignment indicators is missing from the scanning locust;
control a movement of the scanning optic based on a result of the determination that the scanning optic is misaligned;
determine that the scanning optic is aligned with respect to the subject's eye when the plurality of alignment indicators are present in the scanning locus; and
control the scanning optic to irradiate the light to an inner edge portion of a predetermined area on the fundus.

2. The fundus imaging apparatus according to claim 1, wherein, in the alignment mode, the microprocessor is further configured to control a display of the image of the fundus including the plurality of alignment indicators formed by the image forming circuitry on a display.

3. The fundus imaging apparatus according to claim 2, wherein
the scanning optic includes a scanner, and
in the alignment mode, while keeping the light source on, the microprocessor performs control of the scanner based on a scanning locus identical to a scanning locus for forming the image of the fundus in cooperation with control of output timing of a light receiving signal from the light receiver to display the image of the alignment indicator on the display.

4. The fundus imaging apparatus according to claim 1, wherein
the scanning optic includes a scanner, and
in the alignment mode, the microprocessor controls the scanner to form a different scanning locus from a scanning locus for forming the image of the fundus to project the alignment indicator on the fundus.

5. The fundus imaging apparatus according to claim 1, wherein
the scanning optic includes a scanner, and
in the alignment mode, the microprocessor performs control of the scanner based on a scanning locus identical to a scanning locus for forming the image of the fundus in cooperation with control of lighting timing of the light source to project the alignment indicator on the fundus.

6. The fundus imaging apparatus according to claim 1, wherein, in the alignment mode, the light irradiated to the fundus is infrared light.

7. The fundus imaging apparatus according to claim 1, wherein
the operation modes of the microprocessor include a fundus observation mode for observing a moving image of the fundus of the subject's eye, and
in the fundus observation mode, the microprocessor controls the light source such that a fixation target of visible light is presented to the subject's eye.

8. The fundus imaging apparatus according to claim 1, wherein the scanning optic forms a light spot with the light from the light source, scan the fundus with the light spot, and receive return light of the light spot from the fundus by the light receiver, the microprocessor controls the scanning optic such that a scanning locus is formed by the light spot in the fundus, and the image forming circuitry forms a front image of the fundus based on the light receiving signal from the light receiver and a position of the scanning locus formed by the light spot.

9. The fundus imaging apparatus according to claim 1, wherein the scanning optic includes an interference optical system that scans the fundus with measurement light and generate interference light by superposing reference light on return light of the measurement light from the fundus, and receives the interference light by the light receiver, the microprocessor controls the scanning optic such that a scanning locus is formed by the measurement light in the fundus, and the image forming circuitry forms a two-dimensional cross sectional image or a three-dimensional image of the fundus based on the light receiving signal from the light receiver and a position of the scanning locus formed by the measurement light.

* * * * *